United States Patent
Stremmel

(10) Patent No.: US 10,155,041 B2
(45) Date of Patent: Dec. 18, 2018

(54) BACTERIAL PHOSPHOLIPASE INHIBITORS AS MODULATOR OF COLONIC BACTERIAL FLORA

(71) Applicant: Universitaetsklinikum Heidelberg, Heidelberg (DE)

(72) Inventor: Wolfgang Stremmel, Heidelberg (DE)

(73) Assignee: Universitaetsklinikum Heidelberg, Heidelberg (DE)

( * ) Notice: Subject to any disclaimer, the term of this patent is extended or adjusted under 35 U.S.C. 154(b) by 0 days.

(21) Appl. No.: 15/129,814

(22) PCT Filed: Mar. 25, 2015

(86) PCT No.: PCT/EP2015/056326
§ 371 (c)(1),
(2) Date: Sep. 27, 2016

(87) PCT Pub. No.: WO2015/144737
PCT Pub. Date: Oct. 1, 2015

(65) Prior Publication Data
US 2017/0173165 A1    Jun. 22, 2017

(30) Foreign Application Priority Data
Mar. 27, 2014 (EP) .................................... 14162028

(51) Int. Cl.
*A61K 45/06*    (2006.01)
*A61K 47/54*    (2017.01)
*A61K 47/55*    (2017.01)

(52) U.S. Cl.
CPC ............ *A61K 45/06* (2013.01); *A61K 47/544* (2017.08); *A61K 47/55* (2017.08); *A61K 47/552* (2017.08); *A61K 47/554* (2017.08)

(58) Field of Classification Search
CPC ...... A61K 38/00; A61K 45/06; A61K 47/544; A61K 47/55; A61K 47/552; A61K 47/554
(Continued)

(56) References Cited

U.S. PATENT DOCUMENTS

| 6,110,933 A | 8/2000 | Takase et al. |
| 2001/0024658 A1* | 9/2001 | Chen ..................... A61K 9/1075 424/452 |

(Continued)

FOREIGN PATENT DOCUMENTS

| DE | 102005045152 A1 | 3/2007 |
| EP | 0465913 B1 | 9/1997 |

(Continued)

OTHER PUBLICATIONS

International Search Report of the International Searching Authority for International Application No. PCT/EP20151056326 dated Jul. 17, 2015.

(Continued)

*Primary Examiner* — Jana A Hines
(74) *Attorney, Agent, or Firm* — Taylor English Duma LLP; Siegfried J. W. Ruppert

(57) ABSTRACT

The present invention relates to the field of gastroenterology and, more particular, to the field of intestinal diseases. More specifically, it concerns uses and methods for the treatment of inflammatory bacterial diseases of the intestine. In particular, it relates to diseases that are associated with bacterial invasion of the intestinal mucus, including, inflammatory bowel diseases, and infectious bacterial diseases. Therefore, the present invention provides agents, a pharmaceutical composition and a kit for treating said diseases. It further relates to a use and a method for treating invasive bacterial diseases of the large intestine.

13 Claims, 3 Drawing Sheets

(58) Field of Classification Search
USPC ............ 514/1.2, 12.2, 15.1, 56, 57, 78, 114; 424/450
See application file for complete search history.

(56) References Cited

U.S. PATENT DOCUMENTS

| | | | | |
|---|---|---|---|---|
| 2004/0229842 | A1* | 11/2004 | Yedgar | C07F 9/10 514/54 |
| 2005/0075345 | A1 | 4/2005 | Heymans et al. | |
| 2007/0117779 | A1 | 5/2007 | Yedgar et al. | |
| 2008/0166401 | A1* | 7/2008 | Stremmel | A61K 31/685 424/450 |

FOREIGN PATENT DOCUMENTS

| | | | | |
|---|---|---|---|---|
| GB | 2346885 B | | 4/2003 | |
| WO | WO 99/44604 | | 9/1999 | |
| WO | WO 2007/064741 A2 | | 6/2007 | |
| WO | WO 2009/137821 | * | 11/2009 | ............ A61K 38/00 |
| WO | WO 2012/073245 A1 | | 6/2012 | |

OTHER PUBLICATIONS

Written Opinion of the International Searching Authority for International Application No. PCT/EP2015/056326 dated Jul. 17, 2015.
Anderson, A. C., "The Process of Structure-Based Drug Design," *Chem & Biol*, (2003), vol. 10, pp. 787-797.
Bhat, M. K. et al., "Simplified methods for the synthesis of 2-hexadeconylthio-1-ethylphosphorylcholine and for the determination of phospholipase $A_2$ activity," *Biochim Biophys Acta*, (1993), vol. 1166, pp. 244-250.
Chamulitrat, W. et al., "Bile Salt-Phospholipid Conjugate Ursodeoxycholyl Lysophosphatidylethanolamide as a Hepatoprotective Agent," *Hepatology*, (2009), vol. 50(1), pp. 143-154.
Chamulitrat, W. et al., "Hepatoprotectant ursodeoxycholyl lysophosphatidylethanolamide increasing phosphatidylcholine levels as a potential therapy of acute liver injury," *Front Phys*, (2012), vol. 3(24), pp. 1-8.
Guo, W. et al., "Phospholipid impregnation of abdominal rubber drains: resistance to bacterial adherence but no effect on drain-induced bacterial translocation," (1993), *Res Exp Med*, vol. 193(5), pp. 285-296.
Hicks, A. M. et al., "Unique molecular signatures of glycerophospholipid species in different rat tissues analyzed by tandem mass spectrometry," (2006), *Biochim. Biophys. Acta.*, vol. 6, pp. 1022-1029.
Hills, B. A., "Gastric mucosal barrier: evidence for *Heliobacter pylori* ingesting gastric surfactant and deriving protection from it," (1993), *Gut*, vol. 34, pp. 588-593.
Hills, B. A., "Surface-acting phospholipid: a Pandora's box of clinical applications. Part II. Barrier and lubricating properties," (2002), *Intern. Med. J.*, vol. 32, pp. 242-251.
Istivan, T. S. & Coloe, P. J., "Phospholipase A in Gram-negative bacteria and its role in pathogenesis," (2006), *Microbiology*, vol. 152, pp. 1263-1274.
Johansson, M. E. et al., "The two mucus layers of colon are organized by the MUC2 mucin, whereas the outer layer is a legislator of host-microbial interactions," (2011), *Proc Natl Acad Sci U S A.*, vol. 108, Suppl. 1, pp. 4659-4665.
Kramer, R. M. et al., "The $Ca^{2+}$-sensitive Cytosolic Phospholipase $A_2$ Is a 100-kDa Protein in Human Monoblast U937 Cells," (1991), *J Biol Chem*, vol. 266, No. 8, pp. 5268-5272.
Krimsky, M. et al. "Amelioration of TNBS-induced colon inflammation in rats by phospholipase $A_2$ inhibitor," (2003), *Am J Physiol Gastrointest Liver Physiol*, vol. 285, pp. G586-G592.
Linkous, A. & Yazlovitskaya, E., "Cytosolic phospholipase A2 as a mediator of disease pathogenesis," (2010), *Cell Microbiol*, vol. 12(10), pp. 1369-1377.
Matoba, Y. et al., "The Crystal Structure of Prokaryotic Phospholipase $A_2$," (2002), *J Biol Chem*, vol. 277(22), pp. 20059-20069.

Matoba, Y. & Sugiyama, M., "Atomic Resolution Structure of Prokaryotic Phospholipase $A_2$: Analysis of Internal Motion and Implication for a Catalytic Mechanism," (2003), *Proteins: Structure, Function, and Genetics*, vol. 51, pp. 453-469.
Murakami, M. et al., "Secreted phospholipase $A_2$ revisited," (2011), *J Biochem*, vol. 150(3), pp. 233-255.
Nevalainen, T. J. et al., "Conserved domains and evolution of secreted phospholipases $A_2$," (2012), *FEBS Journal*, vol. 279, pp. 636-649.
Nienaber, V. L. et al., "Discovering novel ligands for macromolecules using X-ray crystallographic screening," (2000), *Nat Biotechnol*, vol. 18, pp. 1105-1108.
Oakley, A. J. & Wilce, M. C., "Macromolecular Crystallography as a Tool for Investigating Drug, Enzyme and Receptor Interactions," (2000), *Clin Exp Pharmacol Physiol*, vol. 27, pp. 145-151.
O'Hara, A. M. & Shanahan, F., "The gut flora as a forgotten organ," (2006), *EMBO rep*, vol. 7(7), pp. 688-693.
Ono, T., et al., "Characterization of a novel inhibitor of cytosolic phospholipase $A_2\alpha$, pyrrophenone," (2002), *Biochem J*, vol. 363, pp. 727-735.
Pathil, A. et al., "The synthetic bile acid-phospholipid conjugate ursodeoxycholyl lysophosphatidylethanolamide suppresses TNFα-induced liver injury," (2011), *J Hepatol*, vol. 54, pp. 674-684.
Pathil, A. et al., "The Bile Acid Phospholipid Conjugate Ursodeoxycholyl Lysophosphatidylethanolamide Exerts Anti-Fibrogenic Effects and Inhibits Epithelial-to-Mesenchymal Transition by Blocking TGFβ1/SMAD2/3 Signaling," (2011), *J Hepatol*, vol. 54, p. S52.
Pathil, A. et al., "Ursodeoxycholyl Lysophosphatidylethanolamide Improves Steatosis and Inflammation in Murine Models of Nonalcoholic Fatty Liver Disease," (2012), *Hepatology*, vol. 55, pp. 1369-1378.
Pathil, A. et al., "Comparison of different bile acid-phospholipid conjugates in acute hepatitis," (2012), *Eur J Clin Invest*, vol. 42(2), pp. 130-138.
Reynolds, L. J. et al., "Analysis of Human Synovial Fluid Phospholipase $A_2$ on Short Chain Phosphatidylcholine-Mixed Micelles: Development of a Spectrophotometric Assay Suitable for a Microtiterplate Reader," (1992), *Anal Biochem*, vol. 204, pp. 190-197.
Reynolds, L. J. et al., "1-Hexadecyl-2-Arachidonoylthio-2-deoxy-sn-Glycero-3-Phosphocholine as a Substrate for the Microtiterplate Assay of Human Cytosolic Phospholipase $A_2$," (1994), *Anal Biochem*, vol. 217, pp. 25-32.
Sanders, W. J. et al., "Discovery of Potent Inhibitors of Dihydroneopterin Aldolase Using CrystaLEAD High-Throughput X-ray Crystallographic Screening and Structure-Directed Lead Optimization," (2004), *J Med Chem*, vol. 47, pp. 1709-1718.
Sawai, T. et al., "The effect of phospholipase $A_2$ on bacterial translocation in a cell culture model," (2000), *Pediatr Surg Int.*, vol. 16, pp. 262-266.
Schmiel, D. H. & Miller, V. L., "Bacterial phospholipases and pathogenesis," (1999), *Microbes and Infection*, vol. 1, pp. 1103-1112.
Schneider, H. et al., "Lipid Based Therapy for Ulcerative Colitis—Modulation of Intestinal Mucus Membrane Phospholipids as a Tool to Influence Inflammation," (2010), *Int J Mol Sci*, vol. 11, pp. 4149-4164.
Sidebotham, R. L. et al., "Breakdown of gastric mucus in presence of Heliobacter pylori," (1991), *J Clin Pathol*, vol. 44, pp. 52-57.
Street, I. P., et al., "Slow-and Tight-Binding Inhibitors of the 85-kDa Human Phospholipase $A_2$,"(1993), *Biochem*, vol. 32, pp. 5935-5940.
Sturm, A. et al, "Lisofylline and Lysophospholipids Ameliorate Experimental Colitis in Rats," *Digestion*, (2002), vol. 66, pp. 23-29.
Sugiyama, M. et al., "A Novel Prokaryotic Phospholipase $A_2$," (2002), *J Biol Chem*, vol. 277(22), pp. 20051-20058.
Torres, M. I. & Rios, A., "Current view of the immunopathogenesis in inflammatory bowel disease and its implications for therapy," *W J Gastroent*, (2008), vol. 14(13), pp. 1972-1980.
Triantafillidis, J. K. et al., "Current and emerging drugs for the treatment of inflammatory bowel diseases," *Drug Des Dev Ther*, (2011), vol. 5, pp. 185-210.

(56) References Cited

OTHER PUBLICATIONS

Triggiani, M. et al., "Secretory phospholipases $A_2$ in inflammatory and allergic diseases: Not just enzymes," *J Allergy Clin Immunol,* (2005), vol. 116, pp. 1000-1008.

Turner, J. R., "Intestinal mucosal barrier function in health and disease," (2009), *Nat Rev Immunol,* vol. 9, pp. 799-809.

Willumeit, R. et al., "Phospholipids as implant coatings," *J. Mater Med.,* (2007), vol. 18, pp. 367-380.

Zhang, Y. et al., "Expression, purification, and refolding of active human and mouse secreted group IIE phospholipase $A_2$," *Protein Expr Purif,* (2011), vol. 80, pp. 68-73.

\* cited by examiner

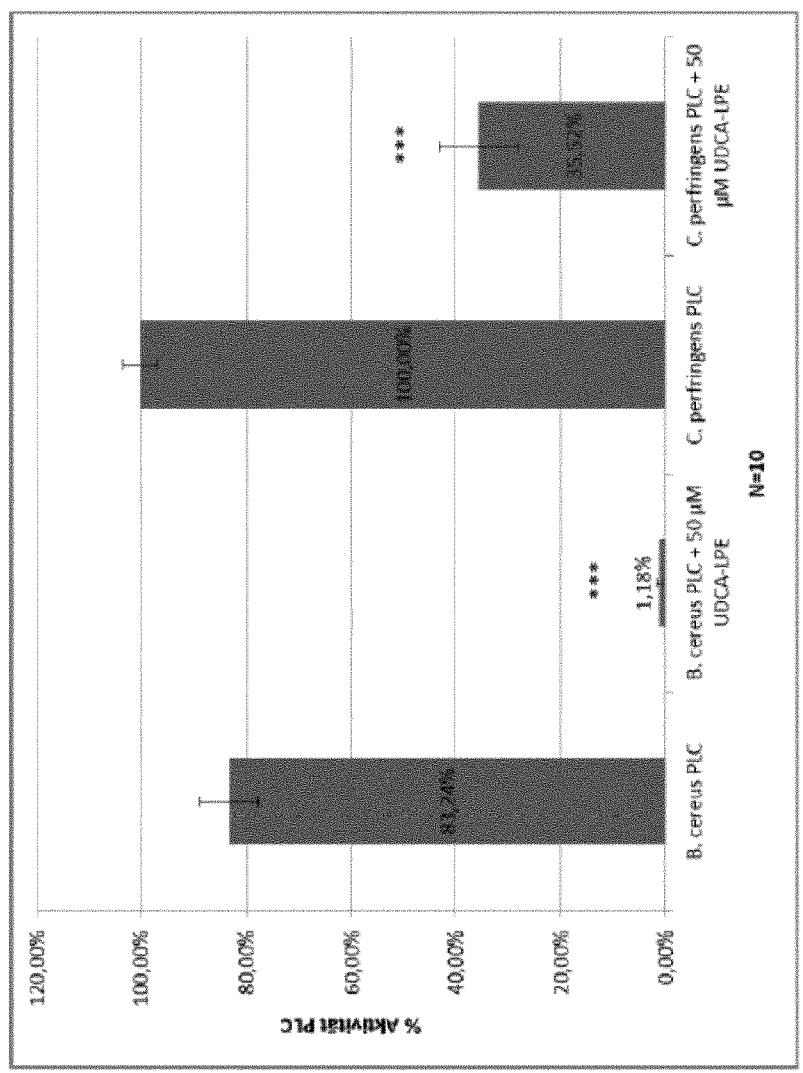

BACTERIAL PHOSPHOLIPASE INHIBITORS AS MODULATOR OF COLONIC BACTERIAL FLORA

BACKGROUND

The intestine is a vital part of the gastrointestinal tract (GIT) that primarily functions to absorb nutrients and water from ingested food and drinks. In consequence, it is constantly exposed to digestive juices, containing enzymes and other agents that act to break down nutrients, dietary antigens and potentially pathogenic microorganisms from the external environment. In addition, the intestine houses the gut flora, myriads of microorganisms from about 500 different species, including bacteria, archaea and eukaryotes.

The mucosa as the innermost layer of the GIT is the interface that is exposed to and interacts with the external environment and the luminal content of the intestine. It consists of epithelial cells forming crypts and villi, subepithelial tissue and lymph nodes (lamina propria), and underneath a continuous sheet of smooth muscle cells (muscularis mucosae). The entire mucosa rests on the submucosa, which consists of a variety of inflammatory cells, lymphatics, autonomic nerve fibers, and ganglion cells. The mucus layer lining the mucosal epithelial cells is the first defensive barrier that protects the underlying mucosa from the entrance of harmful substances or pathogens. Mucus is a complex viscous composition, which typically forms layers surrounding the intestinal lumen. It consists of large glycoproteins, called mucins, which are secreted by specialized epithelial cells and serve as a scaffold for the mucus gel, further containing salts, lipids and proteins (Johansson, et al., 2011) (Turner, 2009). The mucus layer converts the hydrophilic epithelial surface into a hydrophobic "closing seal" that interfaces with luminal contents (Hicks, et al., 2006) (Hills, 2002). Phosphatidylcholines (PC) bind to the negatively charged mucins with their positively charged headgroups while their hydrophobic acyl chains extend to the lumen, thus establishing a high surface tension which normally helps to exclude bacteria from this compartment (Willumeit, et al., 2007) (Guo, et al., 1993).

However, under certain circumstances, bacteria somehow overcome the mucosal barrier of the intestine and elicit intestinal inflammation. Inflammatory bacterial diarrhea is a significant health problem in both developing and developed regions of the world that particularly affects children, elderly persons, and immunosuppressed individuals. The standard treatment is mostly restricted to antibiotics. However, antibiotic therapy is often leveraged by bacterial antibiotic resistances. In addition, antibiotics often elicit severe side effects and can unbalance the gut flora, which may lead to follow-up infections caused by other pathogenic microorganisms.

Intestinal inflammation is also a characteristic of inflammatory bowel diseases (IBD). These chronic, relapsing diseases have been linked to a dysregulated immune response to components of the gut flora. IBD have therefore long been classified as "autoimmune" diseases and are typically treated with anti-inflammatory agents, e.g., corticosteroids, immunosuppressives, antibiotics or even surgical approaches in those who are non-responders to medical treatment. The disadvantages of antibiotic treatment have already been elucidated, and many anti-inflammatory and immunosuppressive agents, too, evoke severe side effects. Surgery should, of course, be the last resort for treatment of IBD (Triantafillidis, et al., 2011).

The exact mechanisms whereby bacteria disrupt and enter the intestinal mucus and the underlying mucosa are still the subject of ongoing research. Despite the differences regarding disease etiology and pathogenesis, the present inventors have identified one common factor shared by many inflammatory intestinal diseases: Bacteria or bacterial antigens cross the natural mucosal barrier and reach the underlying mucosa, where an inflammatory response arises. This understanding lead to the idea to implement treatment at the beginning, i.e. by preventing bacterial invasion of the mucus barrier. And, for the first time, it is herein suggested to do so by inhibiting bacterial phospholipase activity.

Phospholipases (PL) are abundant throughout the prokaryotic and eukaryotic kingdom and constitute a heterogenous group of diverse lipolytic enzymes that share the ability to hydrolyze one or more ester linkages in phospholipids. PL are typically classified based on their site of action; whether they cleave in the hydrophobic diacylglycerol moiety (PLA) or in the polar head group of the amphipathic phospholipid (PLC and PLD). PLAs can be further defined by their positional specificity, i.e. preference for the acyl group attached to position 1 or 2 of the glycerol backbone, as PLA1 and $PLA_2$, respectively; PLBs have both PLA1 and $PLA_2$ activity, i.e., little or no positional specificity (Istivan & Coloe, 2006).

Relatively few studies have elucidated the role of bacterial PL, in particular bacterial $PLA_2$, in host-pathogen interactions. It has been acknowledged that the action of bacterial $PLA_2$ results in the accumulation of free fatty acids and lysophospholipids, which are known to destabilize (host) membranes. Few data suggesting a role in pathogenesis for bacterial PLA, including PLA from *Vibrio parahaemolytics*, *Ricksettia prowazekii* and *Campylobacter coli*, have been linked to hemolytic activity due to the accumulation of lysophospholipids (Schmiel & Miller, 1999) (Istivan & Coloe, 2006). It has further been speculated that bacterial PLA might promote bacterial survival and growth by disrupting innate immune cells, thereby hampering the host's immune defenses, and by providing nutrients in the form of fatty acids for biosynthesis or metabolism. Another option raised was that *Yersinia enterocolitica* PLA may stimulate the pro-inflammatory arachidonic acid cascade by releasing fatty acids, including arachidonic acid, from the glycerol backbone of phospholipids (Schmiel & Miller, 1999). Other studies gave a contradictory picture for bacterial PLA. For example, the injection of *Salmonella newport* into ligated ileal loops induced similar levels of fluid accumulation, desquamation, and mononuclear cell infiltration as the injection of bacteria. In contrast, a PLA mutant strain of *Vibrio cholerae* was reported to induce similar amounts of fluid accumulation in rabbit ligated ileal loops compared to the parent strain. (for review, see (Schmiel & Miller, 1999) (Istivan & Coloe, 2006)).

Even though antibiotics, anti-inflammatory, immunosuppressive and anti-diarrheal agents are available for the treatment of inflammatory bacterial diseases of the intestine, there is still a need for alternative or additional drugs for combating such diseases, because of bacterial resistances to antibiotics, the potential damage of the host's gut flora and the adverse effects.

The technical problem underlying the present invention is to comply with this need. The solution is set out in the claims and the description in aspects and embodiments of the present invention that follow as well as illustrated by the figures and exemplified in the appended examples. To date no therapeutics targeting the detrimental effects of bacterial PLA in diseases affecting the intestine have been developed; as their role of has largely been ignored.

The present inventors, for the first time, present an approach to treat various inflammatory bacterial diseases of the intestine by inhibiting bacterial phospholipases (PL), in particular bacterial $PLA_2$. Of note, therapeutic approaches targeting PLA in inflammatory diseases, and i.a. inflammatory bowel diseases, have focused on inhibiting endogenous host PLA—presumably because host PLA are implicated in a variety of signaling pathways and mechanisms; many of which are of relevance in the pathogenesis of inflammatory diseases (see (Linkous & Yazlovitskaya, 2010), (Murakami, et al., 2011)). For example, one function of host soluble $PLA_2$ ($sPLA_2$) is antimicrobial defense through degradation of bacterial membrane phospholipids (see (Murakami, et al., 2011) for review). An increased host cytoplasmic $PLA_2$ ($cPLA_2$) activity has also been reported in tissues infected with *Mycobacterium tuberculosis, Pseudomonas aeruginosa, Listeria monocytogenes* and *Helicobacter pylori* (see (Linkous & Yazlovitskaya, 2010) for review).

Accordingly, several host $PLA_2$ inhibitors have been developed to inhibit or decrease host $PLA_2$ activity. For example, WO9944604 provides an inhibitor of human non-pancreatic $sPLA_2$ for the treatment of inflammatory diseases, including inflammatory bowel diseases. The approach however ignores the role of gut bacteria implicated in IBD, and provides an anti-inflammatory agent to disrupt the host's immune overreaction to the gut flora, rather than targeting harmful effects of the gut flora itself. Similar approaches have been adopted by, e.g., US2005075345, GB2346885, EP0465913, U.S. Pat. No. 6,110,933.

Interfering with host $PLA_2$ activity, however, poses risks. Host $PLA_2$ are abundant and fulfill a plethora of functions. Hence, drugs inhibiting host $PLA_2$ activity are predestined for eliciting systemic side effects, e.g. by impeding membrane maintenance, signaling and immune defense mechanisms. In fact, targeting host $PLA_2$ may even exacerbate bacterial intestinal diseases, as host secreted $PLA_2$ reportedly participate in host defense by destroying bacterial membranes. Instead of providing just another anti-inflammatory agent that attenuates the host's response to bacterial challenge, the present inventors were the first to specifically target bacterial PL, in particular bacterial $PLA_2$ activity of harmful bacteria, thereby avoiding an impairment of host PLA function. This clearly renders the approach superior to state-of-the-art therapeutics for the treatment of inflammatory bacterial diseases of the intestine.

In contrast to any other approach revealed in the prior art, the present inventors have developed a way to effectively target a key event in the pathogenesis of inflammatory bacterial diseases of the intestine: the invasion of the protective intestinal mucus barrier. As of this writing, efforts have been put into inhibiting host PLA to decrease inflammation and tissue destruction in a variety of inflammatory diseases. The present inventors were the first to understand that bacterial PL, in particular bacterial $PLA_2$, are crucial for the pathogenesis of a vast number of inflammatory bacterial diseases affecting the intestine, and, importantly, that inhibiting bacterial PL, in particular bacterial $PLA_2$, activity offers an elegant solution to the task of providing a therapy that acts adversely neither on the patient, nor on his gut flora.

In addition, the present invention provides lysophospholipid-conjugates as inhibitors of bacterial PL, in particular bacterial $PLA_2$, and, consequently, as potent therapeutics for the treatment of a vast number of inflammatory bacterial diseases of the intestine. Clearly, the ability of lysophospholipid-conjugates to interfere with bacterial PLA could not be foreseen.

UDCA-LPE, being one exemplary lysophospholipid-conjugate according to the present invention, had initially been designed for the delivery of the phospholipid-precursor LPE to the steatotic liver, which typically exhibits low PC/LCP levels that have been linked to an increased $PLA_2$ activity (Chamulitrat, et al., 2009). The hepatoprotective effects of UDCA-LPE have been linked to the inhibition of hepatic $PLA_2$ which, on the one hand, results in disintegration of the fatty acid uptake complex and, on the other hand, suppression of the cytosolic generation of lysophosphatidylcholine (LPC), which in turn results in deactivation of JNK1, a common promoter of fatty acid influx, inflammation and apoptosis (Stremmel & Staffer, 2012) (Stremmel, et al., 2012). Of note, phospholipases are a very diverse group of enzymes. For example, although all, eukaryotic and prokaryotic, $sPLA_2$s share the same catalytic mechanism, there is considerable variation in their sequence identity and structure (Nevalainen, et al., 2012). Hence, the finding that UDCA-LPE interferes with hepatic $PLA_2$ can certainly not be expanded to bacterial PLA. The finding that lysophospholipid-conjugates can effectively decrease bacterial PLA activity and therefore exhibit a significant potential for the treatment of intestinal diseases associated with inflammation and, eventually, bacterial invasion of the mucosal barrier of the intestine, therefore clearly came as a surprise. The present invention offers a new, unexpected way to treat inflammatory intestinal diseases that acts more specific, is less toxic and more convenient than state-of-the-art methods.

SUMMARY

The present inventors have surprisingly discovered that lysophospholipid-conjugates, e.g. the bile-acid phospholipid conjugate UDCA-LPE, act as potent inhibitors of bacterial phospholipase, in particular bacterial $PLA_2$. However, also other bacterial phospholipases, such as phospholipase C (PLC), were shown to be inhibited by, e.g. UDCA-LPE. Bacterial PL, particularly bacterial $PLA_2$, have been suggested to play an important role in the pathogenesis of many diseases affecting the intestine, because they can disrupt the protective mucus lining of the intestinal tract (Sawai, 2000). When bacteria penetrate the mucus, an inflammatory response can be triggered in the underlying mucosa. Lysophospholipid-conjugates of the present invention, such as UDCA-LPE, may preferably consist of two tolerable substrates that naturally occur in the host, and preferably exert fewer side effects than conventional antibiotic or anti-inflammatory therapeutics. In addition, because the lysophospholipid-conjugates of the present invention specifically inhibit harmful bacterial PL, in particular PLA activity, they are less toxic for the beneficial bacteria of the gut flora, and are therefore superior to other antibiotic agents that currently represent the standard for treating many acute inflammatory bacterial diseases of the intestine. Patients with chronic inflammatory diseases affecting the intestine are likewise thought to benefit from treatment with lysophospholipid-conjugates. For example, in inflammatory bowel diseases (IBD), bacterial $PLA_2$ activity of resident gut bacteria is thought to promote the chronic inflammatory response that is typically associated with IBD. The present inventors were the first to acknowledge bacterial PL, in particular bacterial $PLA_2$, activity as a common underlying causative or contributing factor of various acute and chronic inflammatory diseases of the intestine, and to recognize that inhibitors of bacterial PL, in particular bacterial $PLA_2$, are potential therapeutics for the treatment of said diseases.

In fact, the prior art did neither explicitly nor implicitly disclose or teach that bacterial phospholipases are to be inhibited for the treatment of inflammatory bacterial diseases of the intestine in a subject. Though phospholipase inhibitors may have been administered to subjects in the prior art (see Krimsky, 2003, US 2007/0117779 or WO 2012/073245), there is no teaching that a bacterial phospholipase should be inhibited with the aim of treating inflammatory bacterial diseases of the intestine in a subject, particularly invasive inflammatory bacterial diseases of the intestine in a subject. Indeed, the etiology of inflammatory diseases of the intestine that were treated with phospholipase inhibitors in the prior art was and is unknown or incompletely understood. As such, the finding of the present inventor that bacterial phospholipases are to be inhibited allows for a selective treatment regimen in that bacterial phospholipases are to be targeted, thereby allowing the treatment of inflammatory bacterial diseases of the intestine in a subject.

It is an established principle that a sharp line must be drawn between what is in fact made available, and what remains hidden or otherwise has not been made available. In the present case, the prior art failed to make technically available what the present inventor found and what is thus described and reflected herein: inhibition of a bacterial phospholipase paves the way for the treatment of inflammatory bacterial diseases of the intestine in a subject, particularly of invasive inflammatory bacterial diseases of the intestine in a subject. Indeed, as shown in the Examples, bacterial phospholipases, such as $PLA_2$ or PLC, are significantly inhibited. Given the involvement of bacterial phospholipases in the invasiveness of bacteria in the intestine, it is apparent that the inhibition of bacterial phospholipases seems to be a promising way of treating inflammatory bacterial diseases of the intestine in a subject.

Thus, in a first aspect, the present invention relates to an inhibitor of bacterial $PLA_2$, $PLA_1$, PLB, PLC and/or PLD for use in a method of treatment of inflammatory bacterial diseases of the intestine.

In addition, the present inventors pioneered in presenting lysophospholipid-conjugates as potent inhibitors of PL, in particular bacterial $PLA_2$.

Accordingly, in a second aspect the present invention relates to lysophospholipid-conjugates for use in a method of treatment of inflammatory bacterial diseases of the intestine in a subject.

The subject is a mammal, for example a mouse, rat, guinea pig, hamster, rabbit, dog, cat, or primate. Preferably, the subject is a human.

Without wishing to be bound by a specific theory, it is speculated that bacterial PL, in particular bacterial $PLA_2$, promote bacterial invasion of the protective mucus layer lining the intestinal tract, and thereby allow bacterial access to the underlying mucosa, where an inflammatory response can arise. Hence, the present invention further relates to the use of lysophospholipid-conjugates for use in a method of treatment of inflammatory bacterial diseases of the intestine in a subject, wherein the inflammatory bacterial diseases are invasive bacterial diseases.

The mammalian intestine comprises two segments: The small intestine and the large intestine. Many intestinal bacterial diseases particularly affect the large intestine. Therefore, in another aspect, the present invention comprises inhibitors of bacterial PL, in particular bacterial $PLA_2$, preferably lysophospholipid-conjugates, for use in a method of treatment of inflammatory diseases of the intestine, wherein the intestine is the large intestine.

It is envisaged that bacterial PL inhibitors, in particular bacterial $PLA_2$ inhibitors, preferably lysophospholipid-conjugates, can be used for the treatment of a broad spectrum of inflammatory bacterial diseases of the intestine, including acute and chronic inflammatory diseases. It is further envisaged that inhibitors of the invention, and in particular lysophospholipid-conjugates, can be used to treat such diseases when bacterial PLA activity may be a causative or a contributing factor. Such diseases include, but are not limited to, appendicitis, pseudoappendicitis, ulcerative colitis, Crohn's disease, enterhemorrhagic colitis, pseudomembranous colitis, collagenous colitis, lymphocytic colitis, ischaemic colitis, diversion colitis, microscopic colitis, Behçet's disease, indeterminate colitis, diverticulitis, megacolon, toxic megacolon, enterocolitis, and caecitis.

The lysophospholipid-conjugate preferably comprises a lysophospholipid chemically coupled to a carrier. Said carrier is preferably a bile acid. Suitable carrier bile acids include ursodeoxycholate (UDCA) and deoxycholate (DCA). Lysophospholipids as part of the lysophospholipid-conjugate of the present invention can be, preferably, lyso-phosphatidylcholine (LPC) or lysophosphatidyletha-nolamine (LPE).

It is further envisaged that the inhibitor of bacterial PL, in particular bacterial $PLA_2$, which is preferably a lysophospholipid-conjugate, of the present invention is administered together with one or more agents selected from the group of antibiotics, anti-inflammatory agents, immunosuppressive agents and anti-diarrheal agents. The term "administered together" comprises administration of the one or more agents prior to, simultaneously, or after inhibitor of the invention.

It is preferred that the inhibitor of the invention, and in particular the lysophospholipid-conjugate of the present invention inhibits bacterial PL, in particular bacterial $PLA_2$.

In a further aspect, the present invention further relates to a pharmaceutical composition comprising lysophospholipid-conjugates and a pharmaceutical carrier, excipient or diluent. Said pharmaceutical composition is preferably for the treatment of inflammatory bacterial diseases of the intestine. Said pharmaceutical composition can further optionally comprise one or more agents selected from the group of antibiotics, immunosuppressive agents, anti-inflammatory agents and anti-diarrheal agents. In a further aspect, the present invention relates to a kit comprising a lysophospholipid-conjugate, for the treatment of inflammatory bacterial diseases of the intestine. Said kit can further optionally comprise one or more agents selected from the group of antibiotics, immunosuppressive agents, anti-inflammatory agents and anti-diarrheal agents, optionally together with a pharmaceutical carrier, excipient or diluent.

In yet another aspect, the present invention also relates to a method of treatment of inflammatory bacterial diseases of the intestine in a subject in need thereof that comprises a step of administering a therapeutically effective amount of an inhibitor of bacterial PL, in particular bacterial $PLA_2$, preferably a lysophospholipid-conjugate to said subject. Said method can further comprise administering one or more agents selected from the group of antibiotics, anti-inflammatory agents, immunosuppressive agents and anti-diarrheal agents. The agent can be administered prior to, simultaneously, or after the inhibitor of the invention.

In yet another aspect, the present invention also relates to the use of an inhibitor of bacterial PL, in particular bacterial PLA$_2$, which is preferably a lysophospholipid-conjugate, for the manufacture of a pharmaceutical composition for the treatment of inflammatory bacterial diseases of the intestine in a subject.

In yet another aspect, the present invention relates to the use of an inhibitor of bacterial PL, in particular bacterial PLA$_2$, which is preferably a lysophospholipid-conjugate, for the treatment of inflammatory bacterial diseases of the large intestine in a subject.

Also, the present invention relates to a method for the production of a pharmaceutical composition for the treatment of inflammatory bacterial diseases of the intestine in a subject, comprising mixing an inhibitor of bacterial PL, in particular bacterial PLA$_2$, which is preferably a lysophospholipid-conjugate, with a pharmaceutically acceptable carrier, diluent or excipient.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

DESCRIPTION OF THE FIGURES

FIG. 3 Phospholipase C activity in *Clostridium perfringens* and *Bacillus cereus*. It is apparent that bacterial phospholipase A2 is inhibited by an inhibitor of the present invention.

DETAILED DESCRIPTION

Figure 1:
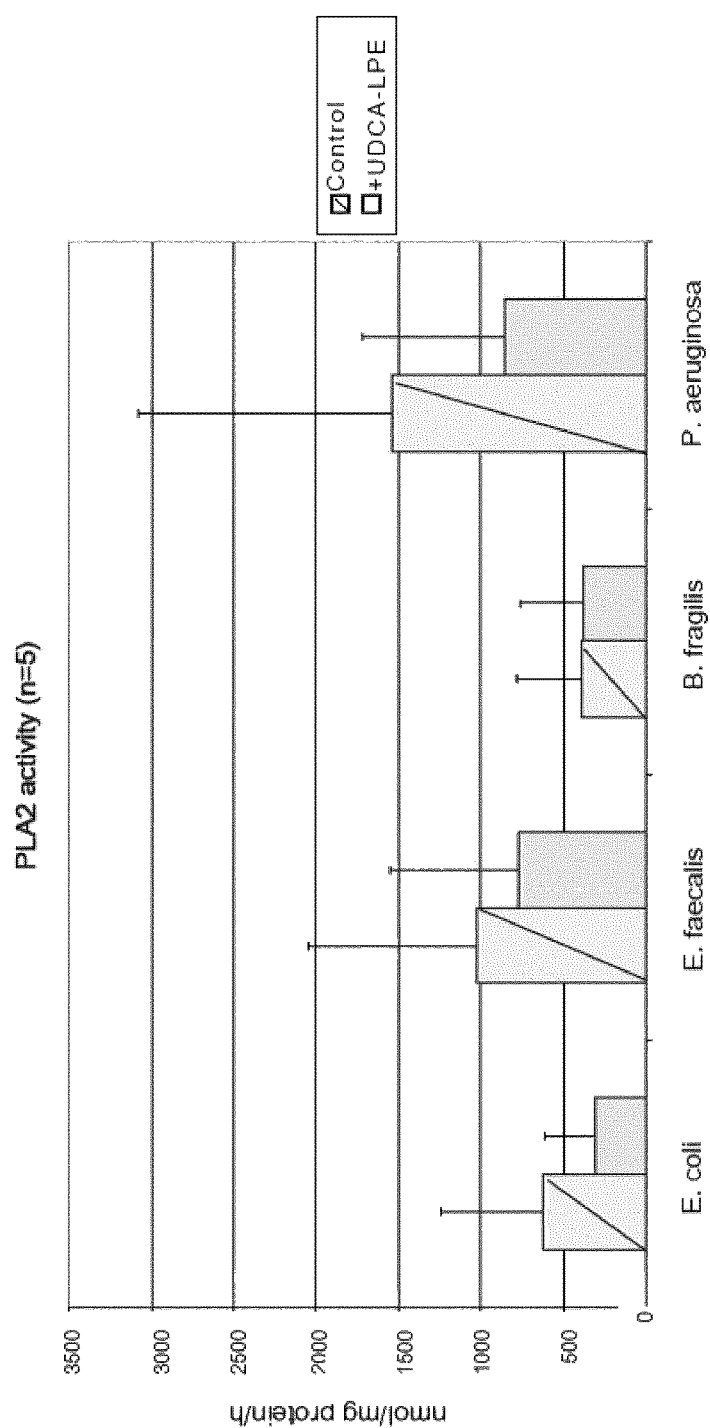
FIG. 1 For determination of phospholipase A$_2$ activity according to Bhat et al. (1993), 10 µl of aliquots of certain isolated bacterial strains prepared from fresh stool samples were incubated with arachidonoyl-thio phosphatidylcholine for 1 hour at 25° C. in a Ca$^{2+}$ free buffer as described herein. The reaction was terminated by 5,5-dithio-bis-2-nitrobenzoic acid. A$_{405}$ was measured and specific PLA$_2$ activity expressed as µmol LPC·mg$^{-1}$ protein·h$^{-1}$ FIG. 2 Phospholipase A$_2$ activity in *Streptomyces violaceoruber*. It is apparent that bacterial phospholipase A2 is inhibited by an inhibitor of the present invention.
Figure 2:
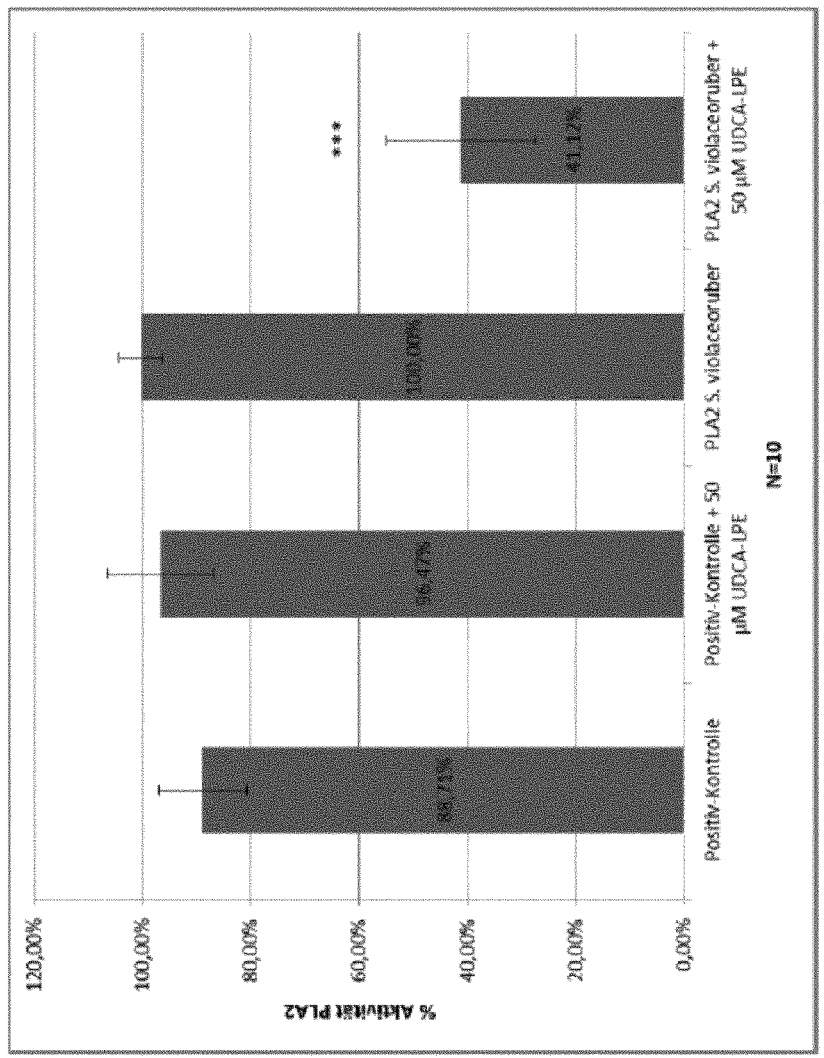

The mucus lines the interface between the gut epithelium and the luminal contents and represents the first line of defense of the intestinal tract. Without wishing to be bound by a specific theory, it is supposed that the activity of bacterial phospholipases, in particular bacterial phospholipases A$_2$, is implicated in various inflammatory intestinal diseases. For example, bacterial PL, in particular bacterial PLA$_2$, can disrupt mucus phospholipids and thereby promote bacterial invasion of the mucus—a scenario that can occur during the course of bacterial infections of the intestine, and which is thought to result in an acute inflammatory response in the intestine. Attempts to control bacterial infections with common antibiotics remain problematic, because bacterial antibiotic resistances are common and still on the rise. In addition, the use of, e.g., broad spectrum antibiotics can unbalance the gut flora, leading for example to overgrowth of harmful bacteria and a reduction of the body's ability to ferment carbohydrates and metabolize bile acids, which often results in antibiotic-associated diarrhea (AAD). Further, antibiotics can cause undesirable side effects in the patient, including abdominal pain, nausea, or hypersensitivity reactions. Bacterial invasion of the intestinal mucus poses a problem not only in infectious bacterial diseases, but is also thought to be of relevance for inflammatory bowel diseases (IBD), which are linked to a dysregulated chronic immune response to the gut flora. IBD are currently treated with corticosteroids or immunosuppressive agents that can elicit severe side effects in the patient. When no response to medical treatment occurs, surgery can be a last option. Controlling bacterial invasion, while at the same time avoiding the use of drugs that are poorly tolerated or even harmful for the patient as well as for beneficial bacteria of the gut flora is therefore a key challenge in the treatment of many diseases affecting the intestine.

The present inventors have strikingly discovered that lysophospholipid-conjugates acting as inhibitors of PLA$_2$, can reduce the activity of bacterial $PLA_2$, enzymes that are suggested as important bacterial virulence factors in the pathogenesis of various inflammatory bacterial diseases of the intestine. It is thought that $PLA_2$ are crucial for bacterial invasion of the mucus and the underlying mucosa. The present inventors have developed the idea that inhibiting bacterial $PLA_2$ activity can be a key step in treating a broad spectrum of inflammatory intestinal diseases which are caused or contributed to by bacteria. Accordingly, in a first aspect, the present invention relates to an inhibitor of bacterial PL, in particular bacterial $PLA_2$, for use in a method of treatment of inflammatory bacterial diseases of the intestine in a subject. Whether or not a particular agent is capable of inhibiting bacterial PL, in particular bacterial $PLA_2$, can be determined by the skilled person, e.g., by the methods described herein.

In principle, in order to identify potential inhibitor of bacterial PL, in particular bacterial $PLA_2$, the person skilled in the art can use the three dimensional structure of bacterial PL or its active site in order to predict which compounds might be inhibitors. Various methods for determining possible ligands have been reviewed by Anderson, 2003. In general, once the target structure has been determined, e.g., by X-ray crystallography, NMR, or homology modeling, computer algorithms can be used to position compounds or fragments thereof from a database into a selected region of the structure. These compounds can be scored and ranked based on their steric and electrostatic interactions with the target site. Such compounds are useful for example as a lead for the development of further analogues, which in turn may have an enhanced inhibitory potential or otherwise beneficial therapeutic properties. On the other hand, the selected compound may bind to a site of the target other than known ligands. Lead compounds can be improved using the 3-D structure of the complex of the lead compound and its biological target. The activity of the selected compound can further be tested with the biochemical assays described herein.

The crystal structure and the tertiary structure of secreted prokaryotic $PLA_2$ (EC 3.1.1.4) from *Streptomyces violaceoruber* A-2688 have been determined by NMR and X-ray analyses (Matoba, et al., 2002) (Matoba & Sugiyama, 2003). It is envisaged that the 3-D structure of *S. violaceoruber* allows an evaluation of bacterial $PLA_2$ inhibitors. Accordingly, computer-aided methods can be used to identify candidate inhibitors for bacterial $PLA_2$. Said methods are further classified into at least three categories: inspection, virtual screening, and de novo generation. In the first category, inspection, known molecules that bind the site, such as substrates or cofactors, are modified to become inhibitors based on maximizing complementary interactions in the target site. Initially, the crystal structure is solved in the presence of a substrate, cofactor, or drug lead. Then, modifications to direct the small molecule toward being a potent inhibitor are designed in silico based on the interactions of the molecule with the target site. The newly designed compounds are then scored for binding using evaluative scoring algorithms available in virtual screening methods.

In virtual screening, databases of available small molecules are docked into the region of interest in silico and scored based on predicted interactions with the site, e.g. shape complementarity or estimated interaction energy. For de novo generation small fragments of molecules, such as benzene rings, carbonyl groups, amino groups, etc., are positioned in the site, scored, and linked in silico. Some programs, e.g., LUDI, are capable of docking fragments of compounds as well as entire compounds, and can thus be used for virtual screening and de novo generation, respectively. Suitable screening tools that can be used to find bacterial $PLA_2$ inhibitors include DOCK, FlexX, FlexE, LUDI and Legend (see Anderson (2003) for other suitable programs).

In view of the fact that bacterial $PLA_2$ was crystallized, the known bacterial $PLA_2$ crystal can also be used in X-ray crystallography-driven screening technique that combines the steps of lead identification, structural assessment, and optimization such as described for example in Nienaber, et al., (2000). This crystallographic screening method (named CrystaLEAD) has been used to sample large compound libraries and detecting ligands by monitoring changes in the electron density map of the crystal relative to the unbound form. The electron density map yields a high-resolution picture of the ligand-enzyme complex that provides key information to a structure-directed drug discovery process. The bound ligand is directly visualized in the electron density map. Ligands that bind way off the target site may be eliminated. The above described methods can be combined with state-of-the-art laboratory data collection facilities including CCD detectors and data acquisition robotics.

The above-mentioned methods can be used to assess the inhibitory potential of a given compound on bacterial $PLA_2$, and/or to identify candidate bacterial $PLA_2$ inhibitors from a library. Once a compound has been identified as a candidate inhibitor by the above methods, its inhibitory effect on bacterial $PLA_2$ may be tested by the method described in the appended example.

Analogous methods can be employed in order to find inhibitors of bacterial phospholipases $A_1$, B, C and D.

It is preferred that the inhibitors of the invention act on bacterial phospholipases, but not on host phospholipases.

Some bacterial phospholipase inhibitors, such as UDCA-LPE, stay within the intestinal lumen of the host and do not enter/are not absorbed by the host mucosal epithelial cells in a considerable amount. Thus, such inhibitors primarily act on bacterial PL, in particular bacterial $PLA_2$, but not on host PL.

It is also conceivable that the bacterial phospholipase inhibitors selectively inhibit bacterial phospholipases, but not host phospholipases. A "host" is a subject affected by the condition to be treated with the inhibitor of the invention. The term "host PL", in particular "host $PLA_2$" includes without limitation secreted and cytosolic forms of PL, in particular $PLA_2$.

The inhibitory effect of a specific compound on host PL, such as host $PLA_2$, can easily be determined by the skilled person by using routine methods known in the art. Various assays, including enzyme assays and cell-based assays, for testing host $PLA_2$ activity have been described, e.g., by Ono, et al., (2002). Exemplary enzyme assays for assessing, e.g., human cytosolic $PLA_2$ activity, include, without limitation, the phosphatidylcholine (PC)/Triton assay according to Street, et al., (1993), modified by Ono et al. (2002), the chromogenic assay according to Reynolds, et al., (1994) and the PC/DOG assay according to Kramer, et al., (1991). Human $sPLA_2$ activity can for example be measured using diheptanoyl thio-PC as a substrate according to Reynolds, et al., (1992). In principle, all methods provide phospholipid-substrates and assess their conversion due to PLA activity.

Many mammalian PLAs are commercially available and can be used in the above-mentioned assays to determine the inhibitory potential of a specific compound. For example, recombinant secretory human $PLA_2$ can be purchased from, e.g., R&D systems and Cayman Chemicals, or can be produced in, e.g., *E. coli* following the protocol of Zhang, et al., (2011).

Cell-based assays for assessing human $PLA_2$ activity employ, for example, thrombin-stimulated platelets, calcium-ionophore-stimulated monocytes (e.g., THP-1, see Ono et al. 2002) or interleukin-1α stimulated human mesangial cells. Fatty acids including arachnidonic acid, prostaglandin or leukotriene from stimulated cells are extracted, and quantified, e.g. by HPLC or by using radioimmunoassay kits or enzyme immunoassay kits.

Ready-to-use kits for determining enzyme activity of mammalian PLA in the presence of a candidate inhibitor are also commercially available, e.g., from Cayman Chemicals ($sPLA_2$ (Type V) Inhibitor Screening Assay Kit) and Invitrogen (EnzChek® Phospholipase $A_2$ Assay Kit).

However, it is also envisaged that the inhibitors of the invention inhibit bacterial $PLA_1$, PLB, PLC and/or PLB. Methods for assessing the inhibitory potential of a specific compound on bacterial $PLA_1$, PLB, PLC and/or PLB are available in the prior art.

In particular, the present inventors have discovered that lysophospholipid-conjugates are potent bacterial phospholipase $A_2$ inhibitors. Phospholipase $A_2$ is thought to play an important role in intestinal inflammation associated with bacteria. Thus, in one aspect, the present invention relates to lysophospholipid-conjugates for the treatment of inflammatory bacterial diseases of the intestine.

The novel treatment according to the present invention is envisaged for a mammal, which can be, for instance, a mouse, rat, guinea pig, hamster, rabbit, dog, cat, or primate. Preferably, the subject is a human.

The present inventors were the first to provide lysophospholipid-conjugates for the treatment of inflammatory bacterial diseases of the intestine as described herein. The term "lysophospholipid-conjugate" as used herein refers to lysophospholipids that are chemically coupled to a carrier. The term "chemically coupled" means, e.g., covalently coupled. However, any other chemical bond is also conceivable. Lysophospholipids (LPL) are naturally derived from phospholipids, such as phosphatidylcholine (PC), phosphatidylethanolamine (PE), phosphatidic acid (PA), phosphatidylserine (PS), phosphatidylinositol (PI) or other phospholipids. Lysophospholipids can, for example, be the result of phospholipase A-type enzymatic activity on phospholipids. Phospholipids are typically composed of two fatty acids, a glycerol unit, a phosphate group and a polar molecule such as, e.g., choline in phosphatidylcholine, or ethanolamine in phosphatidylethanolamine. In contrast, lysophospholipids typically comprise only one fatty acid. In general, any lysophospholipid can be used in the lysophospholipid-conjugate according to the present invention. Suitable lysophospholipids include, but are not limited to, lysophosphatidate, lysophosphatidylethanolamine, lysophosphatidylcholine, lysophosphatidylserine, lysophosphatidylinositol, lysophosphatidylinositolphosphate, lysophosphatidylinositolbisphosphate, lysophosphatidylinositoltriphosphate. In one preferred embodiment, the lysophospholipid is lysophosphatidylethanolamine or lysophosphatidylcholine. It is also envisaged that a phospholipid-conjugate can be used for the treatment of the diseases described herein. The phospholipid could, for example, be phosphatidic acid (phosphatidate), phosphatidylethanolamine (PE), phosphatidylcholine (PC), phosphatidylserine (PS), phosphatidylinositol (PI), phosphatidylinositol phosphate (PIP), phosphatidylinositol bisphosphate (PIP2) or phosphatidylinositol triphosphate (PIP3).

Suitable carriers are, for example, bile acids. However, it is also envisaged that other carriers may be used.

In general, any lysophospholipid and any carrier can be selected to yield the lysophospholipid-conjugate of the invention. The lysophospholipid-conjugate should preferably have capabilities that are similar to the capabilities of the lysophospholipid-conjugate which are evaluated in the appended examples. For example, the lysophospholipid-conjugate of the present invention is preferably capable of inhibiting bacterial PL, in particular bacterial $PLA_2$ activity. The skilled practitioner readily knows how to determine the inhibitory effect of a specific lysophospholipid-conjugate on bacterial an PL, in particular bacterial $PLA_2$, by methods known in the art, e.g., by the method described by Bhat et al. (1993) and in the appended examples.

The selected carrier can be, or can be derived from, a naturally occurring component. Bile acids are steroid acids that are naturally found in the mammalian bile. Primary bile acids, such as, e.g. cholate, are naturally synthesized in the liver and secreted into the lumen of the intestine, where intestinal bacteria chemically convert them to form the secondary bile acids such as, e.g., deoxycholic acid. Suitable bile acids include, but are not limited to, cholic acid, chenodeoxycholic acid, deoxycholic acid, lithocholic acid, glycocholic acid, taurocholic acid, ursodeoxycholic acid. In one preferred embodiment, the bile acid is ursodeoxycholic acid (UDCA) or deoxycholic acid (DCA). It is also envisaged that chemically modified bile acids can be used as carriers in the present invention.

In view of the above, preferred embodiments of the invention thus involve the use of UDCA-LPE, UDCA-LPC, DCA-LPE and DCA-LPC for the treatment of the diseases described herein. However, as already mentioned, other carriers can be used as well to yield the lysophospholipid-conjugates of the present invention. It is in particular envisaged that UDCA-LPE, UDCA-LPC, DCA-LPE and DCA-LPC are formulated in their acidic (i.e., protonated) form.

By inhibiting bacterial PL, in particular bacterial $PLA_2$, it is contemplated the inhibitors of the invention, which are preferably lysophospholipid-conjugates, prevent or decrease bacterial invasion of the intestinal mucus, an event that may eventually result in inflammation of the underlying mucosa. Accordingly, it is envisaged that the inhibitor of the invention, preferably a lysophospholipid-conjugate, is used for treating inflammatory bacterial diseases of the intestine, preferably in a mammal. The inflammatory bacterial diseases to be treated according to the present invention can in particular be invasive inflammatory bacterial diseases.

The mammalian intestine is the part of the alimentary canal extending from the pyloric sphincter of the stomach to the anus. It consists of two parts: the small intestine and the large intestine. It is to be noted that "diseases of the intestine" is to be understood herein as diseases affecting primarily the intestine, but not necessarily limited to the intestine, i.e. the expression also comprises diseases that affect further parts of the body besides the intestine, for example another part of the gastrointestinal tract. In humans, the small intestine is further subdivided into the duodenum, jejunum, and ileum. The "large intestine" is the posterior section of the intestine, and consists of four regions: the cecum, colon, rectum, and anus. The colon the longest segment of the large intestine and houses a large proportion of the gut flora. Many diseases of the intestine affect the large intestine, which in turn often involve the colon.

The expression "invasion" when used herein is to be understood in its broadest sense and, in the context of the present invention, includes one or more of the following:

bacterial damaging, disrupting, penetrating and/or crossing of the intestinal mucus. It can further involve bacterial spread in the invaded mucus, and possibly the underlying mucosa. Accordingly, "invasive" means associated with bacterial damage, disruption, penetration, crossing of and/or bacterial spread in the intestinal mucus and/or mucosa. Without wishing to be bound by a specific theory, it is assumed that bacterial PL, in particular bacterial $PLA_2$, promote bacterial invasion of the intestinal mucus and are pivotal factors in the pathogenesis of many inflammatory bacterial diseases of the intestine.

The mucus lining the intestinal tract has an essential barrier function in the intestine. In the large intestine, it is organized in two layers: an inner, stratified mucus layer that adheres to the underlying epithelial cells; and an outer, nonattached layer. The inner mucus layer is dense and does usually not allow bacteria to penetrate, thus keeping the mucosal epithelial cell surface free from bacteria. The inner mucus layer transitions the outer layer, which harbors the gut flora. Accordingly, bacterial invasion in the large intestine involves invasion of both mucus layers, in particular the inner mucus layer. Mucus typically comprises mucus glycoproteins (also referred to as mucins), that serve as a scaffold for the mucus gel. The mucus gel further typically comprises water, inorganic salts, lipids and further proteins (Johansson, et al., 2011). Phosphatidylcholines are thought to be relevant mucus components. Without wishing to be bound by a specific theory, it is speculated that phosphatidylcholines bind to the mucins with their polar hydrophilic headgroup and extend their hydrophobic fatty acid tails towards the lumen, thereby constituting a hydrophobic barrier that usually prevents bacteria from invading the mucus.

It is further suggested that bacterial PL, in particular bacterial $PLA_2$, may play a pivotal role in bacterial invasion of the intestinal mucus by cleaving mucus phospholipids and thereby compromising the protective features of the mucus. For example, cleavage of mucus phosphatidylcholines may result in distortion of its hydrophobic, exclusive features. Bacterial PL, in particular bacterial $PLA_2$, may further, in a second step, impair the membrane integrity of the mucosal epithelial cells once they have crossed the mucus barrier.

Bacterial phospholipases are a group of enzymes that catalyze the cleavage of phospholipids and are classified in four major groups (A, B, C and D) based on the site of cleavage of their substrates. Bacterial phospholipases A (PLA) and B (PLB) hydrolyze a fatty acid from the phospholipid glycerol backbone, thereby yielding a lysophospholipid. PLA can be further defined by their positional preference for the acyl group attached to position 1 or 2 of the phospholipid glycerol backbone as $PLA_1$ and $PLA_2$, respectively. The present inventors have recognized that bacterial $PLA_2$ are involved in the bacterial invasion of the intestinal mucus which can ultimately result in acute or chronic inflammation, thus contributing to the pathogenesis of a plethora of inflammatory intestinal diseases. The present inventors have further acknowledged that lysophospholipid-conjugates can be used to inhibit bacterial PL, in particular bacterial $PLA_2$, activity. Hence, the lysophospholipid-conjugates according to the present invention preferably inhibit bacterial PLA, and more preferably they inhibit bacterial $PLA_2$.

It is also conceivable that the lysophospholipid-conjugates of the invention, for example UDCA-LPE or any other lysophospholipid-conjugate, inhibit bacterial phospholipases $PLA_1$, PLB, PLC or PLD. Without wishing to be bound by a specific theory, it is speculated that UDCA-LPE may bind to a common specific enzymatic pocket residing in several types of phospholipases which may result in inhibition of the enzymatic activity.

The term "PL" is used herein to refer to phospholipase and applies both for the singular and the plural form. The term "PLA" is used herein to refer to phospholipase A, and applies both for the singular and the plural form. The same is applicable for "$PLA_1$" and "$PLA_2$", respectively. Notably, unless indicated otherwise, when the terms "PLA", "$PLA_1$", "$PLA_2$" are used herein they refer to bacterial phospholipases A, $A_1$ and $A_2$, respectively.

In general, bacterial invasion and/or inflammation can occur at any time point during the course of the disease. E.g., when bacteria penetrate the intestinal mucus and bacterial antigens reach the underlying mucosa, an inflammatory response can be triggered. Inflammatory bacterial diseases of the intestine comprise, i.a., inflammatory bowel diseases (IBD). IBD are a group of chronic diseases typically associated with inflammation of the intestinal tract. The etiology of IBD is not completely understood, however, pathogenesis has been linked to a dysregulated immune response to elements of the intestinal tract. IBD are therefore also referred to as autoimmune disorders. Meanwhile, there is evidence suggesting that chronic inflammation in IBD is, at least in part, caused by an overreaction of the host's immune system to the gut flora. The present inventors have suggested that bacterial PL, and in particular bacterial $PLA_2$, contribute to IBD pathogenesis, e.g. by consuming mucus PC below a borderline level in an individual that already exhibits decreased mucus PC levels. When the mucus barrier is impaired, bacteria can penetrate the mucus and evoke an inflammatory response the underlying mucosa. IBD are typically characterized by periods of clinical exacerbation and remission, with periods of improvement followed by relapse. It is envisaged that lysophospholipid-conjugates of the invention can be used for the treatment of IBD during any of the aforementioned phases. IBD comprise, but are not limited to, Crohn's disease (CD) and ulcerative colitis (UC). Other diseases such as collagenous colitis, lymphocytic colitis, ischaemic colitis, diversion colitis, Behçet's disease and indeterminate colitis are also sometimes classified as IBD. Treatment of said diseases with inhibitors of bacterial PL, and in particular bacterial $PLA_2$, preferably lysophosphatidyl-conjugates, is also envisaged.

The use of the inhibitors of the invention, which are, preferably, lysophospholipid-conjugates, is however not restricted to the treatment of inflammatory bowel diseases. Other diseases that are envisaged for lysophospholipid-conjugate treatment according to the present invention include bacterial infectious diseases, also referred to herein as bacterial infections, of the intestine. Such diseases can occur when pathogenic bacteria enter the intestine and penetrate the mucus, which typically results in inflammation. Further, potentially pathogenic bacteria can already be present in the gut, and, for example as a result of an unbalanced gut flora that fails to suppress their excessive growth, become prevalent. This scenario can arise, e.g., after the use of broad-spectrum antibiotics that act on and interfere with the gut flora. Examples for pathogenic bacteria that can cause an inflammatory infection of the intestine include, but are not limited to, *Shigella, Salmonella, Campylobacter, Clostridium difficile*, and *Escherichia coli* species. It is suggested that such pathogenic bacteria may use bacterial PL, in particular bacterial $PLA_2$, to penetrate the protective mucus, which typically results in inflammation. Thus, infectious inflammatory bacterial diseases, such as (infectious) colitis, enterocolitis and pseudomembranous colitis, are also envisaged for lysophospholipid-conjugate treatment.

In general, the use of and the inhibitors of the invention, in particular, lysophospholipid-conjugates, is further thought to be of benefit in the treatment of any intestinal diseases that is associated with inflammation, but may not initially be caused by bacteria. For example, when the intestinal mucosa is inflamed, it is thought that preventing the detrimental action of bacterial PL, in particular bacterial $PLA_2$, on the protective mucus barrier by the use of the inhibitors of the invention, in particular, lysophospholipid-conjugates, can help to avoid and/or reduce additional tissue damage and inflammation.

The finding that lysophospholipid-conjugates such as UDCA-LPE can inhibit bacterial PL, in particular bacterial $PLA_2$, activity and, therefore, prevent bacteria from invading the intestinal mucus, is, in itself, highly relevant. However, without wishing to be bound by a specific theory, it is further speculated that treatment with the inhibitors of the invention and, in particular, lysophospholipid-conjugates might even favor harmless and/or beneficial bacteria of the gut flora and thereby shift the bacterial spectrum in the intestine towards more tolerable, less invasive bacterial strains. The inhibition of bacterial phospholipases may therefore be selective for specific bacterial strains whereas other strains may not be affected. Therefore a selection process for specific non-invasive bacterial species could be assumed, while pathogenic or tissue-destructing bacterial species carrying phospholipases are reduced. This could be for example important with regard to chronic inflammatory diseases of the intestine, such as IBD, wherein a gut flora exhibiting a low phospholipase activity could potentially outgrow more invasive bacterial species, and prevent re-colonization with invasive species by competitive exclusion, i.e., by consuming nutrients and space. This might break the cycle of recurrent mucus invasion and dysregulated immune response. The selection of specific bacterial strains could further be used to modulate the milieu within the intestinal lumen by inhibiting or stimulating the production of bacterial derived products which have an impact on human metabolism. This could be used, e.g. to suppress bacterial derived ammonium generation in small and large intestine which has an impact for induction of hepatic encephalopathy in end stage disease, liver failure or portal hypertension. Thus, these conditions can be treated. Moreover, the generation of the proatherogenic metabolites of phosphorylcholine-containing food constituents or drugs, e.g. trimethyl-amine-N-oxide (TMAO) could be suppressed by the employed bacterial phospholipase inhibitors such as UDCA-LPE, thereby treating rheumatoid arthritis (RA), since TMAO is suspected to be involved in the etiology of RA.

In contrast to anti-inflammatory and immunosuppressive drugs commonly prescribed for IBD, the inhibitors of the invention and, in particular, lysophospholipid-conjugates, may protect the integrity of the intestinal mucus as a first line defense mechanism, instead of suppressing the host's immune response to an ongoing bacterial invasion.

Accordingly, lysophospholipid-conjugates can be used for the treatment of diseases selected from the group including, but not limited to, appendicitis, pseudoappendicitis, ulcerative colitis, Crohn's disease, enterhemorrhagic colitis, pseudomembranous colitis, collagenous colitis, lymphocytic colitis, ischaemic colitis, diversion colitis, microscopic colitis, Behçet's disease, indeterminate colitis, diverticulitis, megacolon, toxic megacolon, enterocolitis and caecitis.

Pharmaceutically Acceptable Salts

For the purpose of the invention, the inhibitors as defined herein also include the pharmaceutically acceptable salt(s) thereof. The phrase "pharmaceutically acceptable salt(s)", as used herein, means those salts of inhibitors of bacterial PL, in particular bacterial $PLA_2$, inhibitors that are safe and effective for the desired administration form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The use of salt formation as a means of varying the properties of pharmaceutical compounds is well known and well documented. Salt formation can be used to increase or decrease solubility, to improve stability or toxicity and to reduce hygroscopicity of a drug product. There are a wide range of chemically diverse acids and bases, with a range of pKa values, molecular weights, solubilities and other properties, used for this purpose. Of course, any counter-ions used in pharmaceuticals must be considered safe, and several lists of pharmaceutically approved counter-ions exist, which vary depending on the source. Approved salt formers can e.g. be found in the Handbook of Pharmaceutical Salts (Stahl P H, Wermuth C G, editors. 2002. Handbook of pharmaceutical salts: Properties, selection and use. Weinheim/Zurich: Wiley-VCH/VHCA.). Thus, the present invention also comprises the use of pharmaceutically acceptable salts of the bacterial PLA inhibitors of the invention for the treatment of inflammatory bacterial diseases of the intestine in a subject.

Chemical Modification

It is envisaged that bacterial PLA inhibitors can be provided in any chemical form that ensures that it reaches the site of action, i.e., the intestine.

The bacterial PLA inhibitors of the invention may be chemically modified. Generally, all kind of modifications of bacterial PLA inhibitors are comprised by the present invention as long as they do not reduce or abolish the advantageous capabilities and/or the therapeutic effect of the bacterial PLA inhibitors described herein. In the context with the present invention the term "therapeutic effect" in general refers to the desirable or beneficial impact of a treatment, e.g. amelioration or remission of the disease manifestations. The term "manifestation" of a disease is used herein to describe its perceptible expression, and includes both clinical manifestations, hereinafter defined as indications of the disease that may be detected during a physical examination and/or that are perceptible by the patient (i.e., symptoms), and pathological manifestations, meaning expressions of the disease on the cellular and/or molecular level.

The therapeutic effect of the uses and methods described herein is additionally detectable by all methods and approaches that are established for indicating a therapeutic effect in the treatment of inflammatory bacterial diseases of the intestine. Methods for monitoring the therapeutic effect of bacterial PLA inhibitors include, but are not limited to, assessing the presence blood in stool, the number and species of gut bacteria, evaluating symptoms like fever, abdominal pain, and diarrhea, using endoscopic methods or noninvasive imaging techniques to assess the redness, swelling, mucus condition, and assessing inflammation, e.g., by obtaining tissue samples and screen for inflammatory cytokines, chemokines or others and numbers and types of inflammatory cells.

Additionally or alternatively it is also possible to evaluate the general appearance of the respective patient (e.g., fitness, well-being) which will also aid the skilled practitioner to evaluate whether a therapeutic effect has been elicited. The skilled person is aware of numerous other ways which are suitable to observe a therapeutic effect of the bacterial PLA inhibitors of the present invention.

Thus, a further embodiment of the present invention is the use of bacterial PLA inhibitors which are chemically modified.

Treatment

The term "treatment" in all its grammatical forms includes therapeutic or prophylactic treatment of inflammatory bacterial diseases of the intestine. A "therapeutic or prophylactic treatment" comprises prophylactic treatments that aim at the complete prevention of clinical and/or pathological manifestations or therapeutic treatment which that aims at amelioration or remission of clinical and/or pathological manifestations. The term "treatment" thus also includes the amelioration or prevention of inflammatory bacterial diseases of the intestine.

Dose

The exact dose of bacterial PLA inhibitors will depend on the purpose of the treatment (e.g. remission maintenance vs. acute flare of disease), and will be ascertainable by one skilled in the art using known techniques. As is known in the art and described above, adjustments for route of administration, age, body weight, general health, sex, diet, time of administration, drug interaction, and the severity of the condition may be necessary, and will be ascertainable with routine experimentation by those skilled in the art.

Composition

Bacterial PLA inhibitors, which are preferably lysophospholipid-conjugates, can also be used as part of a pharmaceutical composition. Thus, a further aspect of the invention a pharmaceutical composition comprising lysophospholipid-conjugates for the treatment of inflammatory bacterial diseases of the intestine. It is to be acknowledged that the embodiments described in the context of the use of bacterial PLA inhibitors and lysophospholipid-conjugates are equally applicable to the pharmaceutical composition of the invention, mutatis mutandis. The pharmaceutical composition may further comprise a pharmaceutically acceptable excipient, carrier or diluent. Processes known per se for producing medicaments are for example indicated in Forth, Henschler, Rummel (1996) Allgemeine und spezielle Pharmakologie und Toxikologie, Urban & Fischer.

Pharmaceutical compositions of the invention comprise a therapeutically effective amount of lysophospholipid-conjugates and can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for topical or oral administration.

By "therapeutically effective amount" is meant an amount of lysophospholipid-conjugate that elicits a therapeutic effect as described herein.

In general, coated dosage forms, e.g., for oral administration, may be a single unit system or a multi-particulate system, and each of these may be a single-layer product or a multi-layer product. In either case, the coating can be applied to a variety of solid core formulations such as tablets, capsules, mini tablets, pellets, granules or the like.

Systems for transdermal delivery are fabricated as multilayered polymeric laminates in which a drug reservoir or a drug-polymer matrix is sandwiched between two polymeric layers: an outer impervious backing layer that prevents the loss of drug through the backing surface and an inner polymeric layer that functions as an adhesive and/or rate-controlling membrane. Transdermal drug delivery systems comprise different systems such as the reservoir systems, microreservoir systems, and the combination of reservoir and matrix-dispersion systems.

Reservoir-based drug delivery systems can be used, e.g., for oral, dermal and implantable delivery systems. In the reservoir system, the drug reservoir is embedded between an impervious backing layer and a rate-controlling membrane. The drug releases only through the rate-controlling membrane, which can be microporous or non-porous. In the drug reservoir compartment, the drug can be in the form of a solution, suspension, or gel or dispersed in a solid polymer matrix. On the outer surface of the polymeric membrane a thin layer of drug-compatible, hypoallergenic adhesive polymer can be applied. In the Matrix systems and Drug-in-adhesive system the drug reservoir is formed by dispersing the drug in an adhesive polymer and then spreading the medicated polymer adhesive by solvent casting or by melting the adhesive (in the case of hot-melt adhesives) onto an impervious backing layer. On top of the reservoir, layers of unmedicated adhesive polymer are applied. In the Matrix-dispersion system the drug is dispersed homogeneously in a hydrophilic or lipophilic polymer matrix. This drug-containing polymer disk then is fixed onto an occlusive baseplate in a compartment fabricated from a drug-impermeable backing layer. Instead of applying the adhesive on the face of the drug reservoir, it is spread along the circumference to form a strip of adhesive rim. The drug delivery system is a combination of reservoir and matrix-dispersion systems. The drug reservoir is formed by first suspending the drug in an aqueous solution of water-soluble polymer and then dispersing the solution homogeneously in a lipophilic polymer to form thousands of unleachable, microscopic spheres of drug reservoirs. The thermodynamically unstable dispersion is stabilized quickly by immediately cross-linking the polymer in situ.

Rectal applications can be compounded in many forms. Liquid rectal medicine solutions are given by enema. Creams, lotions and ointments are applied externally or inserted internally using an applicator. Suppositories might be prepared by mixing medicine with a wax-like substance to form a semi-solid, bullet-shaped form that will melt after insertion into the rectum.

Intraperitoneal injection or IP injection is the injection of a substance into the peritoneum (body cavity). A further form of administration of an inventive composition is the topic administration, for instance in form of an ointment or cream. Such an ointment or cream may additionally comprise conventional ingredients, like carriers or excipients as described herein. Lysophospholipid-conjugates can also be used in sprays, for example for inhalation. Lysophospholipid-conjugates may also be added to foods.

The pharmaceutical composition may be administered with a pharmaceutically acceptable carrier, excipient or diluent to a patient, as described herein. In a specific embodiment, the term "pharmaceutically acceptable" means approved by a regulatory agency or other generally recognized pharmacopoeia for use in animals, and more particularly in humans. Accordingly, the pharmaceutical composition may further comprise a pharmaceutically acceptable carrier, diluent or excipient. Generally all carriers are suitable that are pharmaceutically acceptable and enable a release of the lysophospholipid-conjugate at the desired site of action. The person skilled in the art knows which type of carrier is suitable depending on, e.g., the chosen administration route and the target site. For example, carriers in the context with e.g. a rectal application are e.g. multi matrix systems using methacrylic acid copolymers. If e.g. the desired site of action is the colon and the compound as described herein is applied orally the carrier has to be resistant to gastric acid in order to enable a release of the compound as described herein in the colon.

Exemplary pharmaceutically acceptable carriers that are suitable for formulating the composition include (biodegradable) liposomes; microspheres made of the biodegradable polymer poly(D,L-lactic-coglycolic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable carriers and excipients are inter alia described in Remington's Pharmaceutical Sciences, 15$^{th}$ Ed., Mack Publishing Co., New Jersey (1991) and Bauer et al., Pharmazeutische Technologie, 5$^{th}$ Ed., Govi-Verlag Frankfurt (1997).

A variety of routes are applicable for administration of the lysophospholipid-conjugate of the invention, including, but not limited to, orally, topically, transdermally, subcutaneously, intravenously, intraperitoneally, intramuscularly or intraocularly. Of course, any other route may readily be chosen by the person skilled in the art if desired.

In one preferred embodiment, the lysophospholipid-conjugation of the invention is administered orally. Accordingly, the lysophospholipid-conjugate, which preferably released within the intestinal tract, is formulated such that it allows an enteric coating. An enteric coating as used herein refers in general to a coating that controls the location in the digestive system where a drug is released.

Lysophospholipid-conjugates can inhibit bacterial PLA activity, and are therefore considered as a potential drugs for treating inflammatory bacterial diseases of the intestine. In one embodiment, lysophospholipid-conjugates are delivered to and released in the colon. It is within the knowledge of the person skilled in the art to select a pharmaceutical carrier, excipient or diluent that can be used to formulate a delivery system such as, e.g., a colon-targeted drug delivery system.

Suitable delivery systems for intestinal drug delivery, and in particular colonic delivery, have been reviewed by, e.g., Jain and Jain (2008) and Van den Mooter (2006). In general, suitable formulations for intestinal delivery comprise delayed release dosage forms that may be designed to provide a "burst release" or a sustained/prolonged release once they reach the target site. The person skilled in the art is aware that the proper selection of a suitable formulation approach is dependent on several factors, for example pathology of the disease, physicochemical and biopharmaceutical properties of the drug and the desired release profile of the active ingredient. Systems that are particularly suitable for intestinal delivery include prodrugs, pH-dependent delivery systems, time release/delayed systems, microbial-triggered systems, and pressure-dependent systems.

Generally, a prodrug is a composed of a drug and a carrier which are chemically coupled to each other. Upon administration, the moiety preferably maintains its integrity while passing the non-target intestinal parts until it reaches its target, such as, e.g., the colon. On reaching its final destination, the prodrug is then converted into the parent drug molecule. Site-specific drug delivery through site-specific prodrug activation can be accomplished by utilizing a specific property of the target site, e.g. a low pH or the presence of specific enzymes, including host enzymes as well as enzymes of the bacterial gut flora. E.g., when targeting drugs to the colon, a prodrug can be used that is converted into the parental drug via the action of bacterial enzymes of the gut flora, such as azoreductase, glycosidase, polysaccharidases, or cyclodextrinase. This can also be referred to as "microbial-triggered" delivery. Accordingly, prodrug approaches including azo bond prodrugs, glysoside conjugates, glucuronide conjugates, cyclodextrin conjugates, dextran conjugates and amino acid conjugates can be used to target the compound of the invention to the target site. More specifically, pectin, guar gum, inulin, locus bean gum, glucomannan, chitosan, chondroitin sulfate, hyaluronic acid, alginates, dextran, starch, amylase, cellulose, cyclodextrin, curdlan, and sclereoglucan conjugates or mixtures thereof, optionally comprising other polymers, can be used.

The rationale underlying pH-dependent intestinal delivery systems is the use of coating agents that dissolve only at a certain pH range that can be found in a specific part of the intestine. Thus, pH dependent delivery systems exploit the rising of the pH from the stomach to the large intestine. For the purpose of targeting drugs to, e.g., the colon, tablets, capsules or the like can be coated with a pH-dependent polymer that is insoluble at low pH but soluble at neutral or slightly alkaline pH. This would thus preferably release the drug in the colon. Conversely, when the target site lies in the stomach, the person skilled in the art will select a pH-dependent polymer that is insoluble at a high pH but dissolves in the acidic environment of the stomach. Exemplary pH-dependent polymers include, but are not limited to, derivatives of acrylic acid and cellulose such as polyvinyl acetate phtalathe (PVAP, e.g., Coateric®), cellulose acetate trimellitate (CAT), hydroxypropyl methylcellulose phthalate (HPMCP), hydroxypropyl methylcellulose acetate succinate (HPMCAS), methylacrylic acid copolymer (e.g., Eudragit®), and cellulose acetate phthalate (CAP, e.g., Aquateric®). Eudragit® coating is preferred for the delivery of lysophospholipid-conjugates.

Time-dependent delivery systems can also be applied in order to deliver lysophospholipid-conjugates to the intestine. These systems are in general designed to resist the environment of the non-target sites of the intestine and to undergo a silent phase of a predetermined time duration, after which site-specific release of the drug takes place. For example, for colon-targeted drug delivery, the silent phase is the transit time from the mouth to the terminal ileum. Examples for time-dependent delivery systems include, but are not limited to, Pulsincap® and the delayed release osmotic dosage form Oros CT®. Other time-dependent drug delivery systems comprise multiple coated oral dosage forms and enteric-coated time-release press-coated tablets (ETP tablets).

Another approach is the use of pressure-controlled drug delivery capsules (PCDC) that rely on the physiological luminal pressure in the intestine which results from peristalsis for drug release.

Other systems for site-specific drug delivery, in particular to the colon, include the CODES® technology, and the use of recombinant bacteria, e.g., *Lactobacillus sporogenes*, as a live vector system that have been genetically engineered to colonize a specific part of the intestine and produce the desired drug there.

The pharmaceutical composition of the present invention may further comprise one or more additional agents. Preferably, said agents are therapeutically effective for treatment of inflammatory bacterial diseases of the intestine and are selected from the group of antibiotics, immunosuppressive agents, anti-inflammatory agents, and anti-diarrheal agents. Of course, the person skilled will select agents that are therapeutically effective for the treatment of the specific inflammatory bacterial disease of the intestine to be addressed.

The term "antibiotics" is used herein to refer to chemical substances that kill and/or inhibit growth of certain microorganisms, in particular certain bacteria. Antibiotics may be broad-spectrum, i.e. active against a wide range of microorganisms or narrow-spectrum, i.e. active against one specific microorganism, or one specific class of microorganisms. Either one may be used within the pharmaceutical composition or the kit according to the present invention. The term "antibiotics" refers to natural antibiotics (i.e., naturally produced by a microorganism), semisynthetic antibiotics (i.e., natural antibiotic derivatives that have been chemically modified) and fully synthetic antibiotics (i.e., antibiotics that are not of natural origin) can be used in the context of the present invention. Suitable antibiotics for the use according to the present invention include, but are not limited to, penicillins such as penicillin G, penicillin V, benzathine penicillin, methicillin, oxacillin, nafcillin, cloxacillin, dicloxacillin, ampicillin, amoxicillin, carbenicillin, and ticarcillin, mezlocillin, piperacillin, amoxicillin, azlocillin, flucloxacillin; cephalosporins such as cefazolin, cefadroxil, cephalothin, cephalexin, cefazolin, cephalothin, cephaloclor, cefamandole, cefoxitin, cefprozil, cefuroxime, cefdinir, cefditoren, cefoperazone, cefotaxime, cefpodoxime, ceftibuten, ceftizoxime, ceftaroline fosamil, ceftobiprole, ceftriaxone, cefixime, ceftazidime, cefepime; aminoglycosides such as amikacin, gentamicin, kanamycin, neomycin, netilmicin, tobramycin, paromomycin, spectinomycin; glycopeptides such as teicoplanin, vancomycin, telavancin; lincosamides such as clindamycin, lincomycin; lipopetides such as daptomycin; macrolides such as azithromycin, clarithromycin, dirithromycin, erythromycin, roxithromycin, troleandomycin, telithromycin, spiramycin; monobactams such as aztreonam; nitrofurans such as furazolidone, nitrofurantoin; oxazolidonones such as linezolid, posizolid, radezolid, torezolid; ansamycins such as geldanamycin, herbimycin; carbacephems such as loracarbef; carbapenems such as ertapenem, doripenem, iminipem, meropenem; polypeptides such as bacitracin, colistin, polymyin B; quinolones such as ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; sulfonamides such as mafenide, sulfacetamide, sulfadiazine, silver sulfadiazine sulfadimethoxine, sulfamethizole, sulfamethoxazole, sulfasalazine, sulfisoxazole; tetracyclines such as demeclocycline, doxycycline, minocycline, oxytetracycline, tetracycline; broxyquinoline, acetarsol, nifuroxazide, nifurzide, metronidazole.

Other agents that can be comprised within the pharmaceutical composition of the invention include anti-inflammatory agents, immunosuppressive agents, and anti-diarrheal agents.

"Anti-inflammatory agents" inhibit or reduce inflammation, e.g., by inducing the production of anti-inflammatory mediators and/or inhibiting the production of pro-inflammatory mediators. Suitable anti-inflammatory agents for use according to the present invention include glucocorticoids, e.g. cortisone, hydrocortisone (cortisol), prednisone, prednisolone, methylprednisolone, dexamethasone, betamethasone, triamcinolone, beclometasone, fludrocortisone acetate, deoxycorticosterone acetate, budesonide, tixocortol. Immunosuppressive agents inhibit or prevent activity of the immune system, e.g., by inhibiting lymphocyte proliferation. Exemplary immunosuppressive agents suitable for use according to the present invention include, e.g. 5-aminosalicylate (5-ASA), mesalazine, sulfasalazine, olsalazine, balsalazine, azathioprine, mycophenolate, methotrexate, cyclosporine. In addition, the pharmaceutical composition of the invention may further comprise other agents that are hereinafter referred to as "anti-diarrheal agents". Diarrhea is often associated with inflammatory diseases of the intestine. The following agents can be applied to provide relief from diarrhea and are thus are suitable for the treatment of inflammatory bacterial diseases of the intestine: flavonoids, prebiotics, intestinal adsorbents, e.g., charcoal preparations, bismuth preparations, pectin, kaolin, crospovidone, attapulgite, diosmectite, and combinations or derivatives thereof, antipropulsives, e.g., diphenoxylate, opium, loperamide, difenoxin, loperamide oxide, morphine, and combinations or derivatives thereof, cholestyramine, cholestipol, heparin, albumin tannate, ceratonia, calcium compounds, racecadotril, aluminium salicylates, zinc oxide, and oral rehydration salts. Monoclonal antibodies and antibody fragments, e.g., infliximab, natalizumab, can also be used as additional agents in the pharmaceutical composition of the present invention.

Further, probiotics can be used. Probiotics are living microorganisms that upon ingestion in specific numbers have a beneficial effect, e.g., by inhibiting pathogenic bacteria, producing cytokines, exerting anti-inflammatory effects or enhance the digestion and absorption of food. Exemplary probiotics include *Lactobacillus* and *Bifidobacterium* species, *Saccharomyces boulardii*, and *E. coli* Nissle bacteria.

Kit

It is also envisaged by the present invention that lysophospholipid-conjugates can be used as part of a kit. Accordingly, in a further aspect, the present invention also relates to a kit comprising lysophospholipid-conjugates for use in a method of treatment of inflammatory bacterial diseases of the intestine.

The kit may be a kit of two or more parts, and comprises lysophospholipid-conjugates and optionally a pharmaceutically acceptable carrier, diluent or excipient. The components of the kit may be contained in a container or vials. The kit may further comprise one or more agents selected from the group of antibiotics, immunosuppressive agents and anti-inflammatory agents. Suitable agents have been described in the context of the pharmaceutical composition of the invention and are equally applicable for the kit, mutatis mutandis. It is envisaged that the agents are applied simultaneously, or sequentially, or separately with respect to the administration of the lysophospholipid-conjugate. The present invention further encompasses the application of the agents via different administration routes. Therefore, suitable agents for use in the kit further comprise, e.g., intravenously administered glucocorticoids for simultaneous, or sequential, or separate use with an orally administered lysophospholipid-conjugate.

In general, it is envisaged that the lysophospholipid-conjugate of the present invention and the one or more additional agents described herein, when provided in form of the pharmaceutical composition or the kit of the present invention, are used for combination therapy.

Method of Treatment

Another aspect of the present invention is a method of treatment of inflammatory bacterial diseases of the intestine in a subject in need thereof, comprising administering a therapeutically effective amount of an inhibitor of bacterial PL, in particular bacterial $PLA_2$, which is preferably a lysophospholipid-conjugate, to said subject. The person skilled in the art will acknowledge that the embodiments described herein in the context of the use of the bacterial phospholipase A inhibitor, the pharmaceutical composition and the kit of the present invention are also applicable to the method of treatment, mutatis mutandis.

The method according to the present invention may further comprise additional steps that are suitable for treating inflammatory bacterial diseases of the intestine. For example, lysophospholipid-conjugate treatment may be combined with a specific diet, e.g., a restricted or low fibre diet. It is also envisaged that the method of treatment according to the present invention further comprises administering one or more agents selected from the group of antibiotic, anti-inflammatory, immunosuppressive and anti-diarrheal agents. Said agents can be administered prior to, simultaneously, or after the inhibitor of bacterial PL, in particular bacterial $PLA_2$, which is preferably a lysophospholipid-conjugate.

In another aspect, the present invention provides a method of producing of a pharmaceutical composition comprising a lysophospholipid-conjugate. The use of lysophospholipid-conjugates for the preparation of a pharmaceutical composition is another aspect of the present invention.

A better understanding of the present invention and of its advantages will be had from the following examples, offered for illustrative purposes only. The examples are not intended to limit the scope of the present invention in any way.

EXAMPLE 1

Preparation of Bacterial Lysates

Cultivation

Suspensions of the respective bacterial strain in 0.9% NaCl were prepared in Sarstedt tubes and adjusted to 1.0 ($3\times10^8$ CFU/ml) with opacimeter (Densimat® or Densicheck®). Subsequently, a BHI (brain heart infusion, purchased from Merck) was inoculated with 500 µl of the suspension and incubated at 37° C. aerob or in an airtight jar with BD Gas Pak™ for 16 hours overnight on a shaker.

Incubation with Phospholipase Inhibitor

BHI was centrifuged for 10 min at 3000 g. The pellet was resuspended in 1 ml PBS and PL-inhibitor (UDCA-LPE, 100 µM; 5 µl stock (20 mM) in 1 ml) or solvent control (Ethanol) and incubated for 1 hour on the shaker.

Preparation of Bacterial Lysates

The bacterial suspensions were washed twice in 2×PBS (centrifugation for 10 min at 3000 g). The pellet was resuspended in 150 µl 1.5% Triton X-100 (in PBS). Subsequently, 1.5 ml Eppendorf tubes were filled with sterile glass beads in the lower third of the cone and the bacterial suspension was transferred to the Eppendorf tubes and put on ice.

Then, the suspension was homogenized 4×1 min in the bead beater (Biospec®), and put on ice for 1 min after every homogenization step. The suspension was then incubated for 60 min on the shaker on ice and centrifuged for 15 min at 10000 g and 4° C. The supernatant was then removed, put on ice and used for determination of the protein concentration (according to Pierce, Thermo Scientific) and determination of PLA activity.

EXAMPLE 2

Determination of $PLA_2$ Activity $PLA_2$ activity was determined as described by Bhat, et al. (1993).

Reagents

2×$PLA_2$ Assay Buffer

| $Ca^{2+}$-dependent_PI, A2 | $Ca^{2+}$-independent $PLA_2$ |
|---|---|
| 300 mM NaCl | 300 mM NaCl |
| 0.5% Triton X100 | 0.5% Triton X100 |
| 60% glycerol | 60% glycerol |
| 20 mM $CaCl_2$ | 4 mM EGTA |
| 160 mM HEPES, pH 7.4 | 10 mM HEPES, pH 7.4 |
| then added with 2 mg/ml BSA for assay (typically 5 mg BSA/10 ml buffer) | then added with 2 mg/ml BSA for assay (typically 5 mg BSA/10 ml buffer) |

$cPLA_2$ Colour Reagent 5,5'dithiobis-2-nitrobenzoic acid stock (DTNB, FW=396.35 g/m01)→25 mM DTNB in 0.5 M Tris (pH 8.0), 4.75 mM EGTA Assay For substrate preparation, 125 µg substrate arachidonyl PC (AAPC) was pipetted into Eppendorf reaction tubes (therefore, the volume to pipet from AAPC stocks in ethanol as supplied by Cayman Chemicals was calculated). The aliquots were dried with speed vac for 10-15 min at 30° C. and stored at −20° C. Before next use, the pellet was airdried under nitrogen to remove residual ethanol.

Immediately before performing the assay, 125 µg substrate pellet was resuspended in 95 µl 2×$PLA_2$ buffer by vortexing. 95 µl $H_2O$ was added and mixed well by vortexing, thereby yielding 1×$PLA_2$ buffer=190 µl. 10 µl of the sample was pipetted into a 96 well plate and add 190 µl of substrate solution was added. The plate was shaken for 30 sec to mix and covered with a plate cover. The plate was incubated at room temperature for 1 hour. Subsequently 10 µl of 25 mM DTNB stock was added into each well to terminate the reaction, the plate was shaken and incubated for 5 min at room temperature.

Finally, the absorption was read at 405 nm and 595 nm.

Calculation

A unit of $PLA_2$ is defined as a nmol of product formed by 1 ml sample in 1 h incubation. $PLA_2$ activity was determined using the following formula:

$$PLA_2\ activity(unit) = (OD405\ nm - OD_{595}\ nm) \times 78.62 \times 50$$

Wherein 78.62 is the amount of product (nmol) producing $OD_{405}$ nm of 1.0 in 0.2 ml, and 50 is the correction factor for 10 µl of sample to 1 ml.

AAPC at 125 µg per sample in 200 µl gives 1 mM final. One may also use 62.5 µg per sample giving 0.5 mM final concentration (to save material for low activity samples or for sorcening purposes).

CITED LITERATURE

Anderson, A. C., 2003. The Process of Structure-Based Drug Design. *Chem & Biol*, Volume 10, pp. 787-797.

Bhat, M. K., Mueller-Harvey, I., Summer, I. G. & Goodenough, P. W., 1993. Simplified methods for the synthesis of 2-hexadeconylthio-1-ethylphosphorylcholine and for the determination of phospholipase A$_2$ activity. *Biochim Biophys Act*, Volume 1166, pp. 244-250.

Chamulitrat, W. et al., 2009. Bile Salt-Phospholipid Conjugate Ursodeoxycholyl Lysophosphatidylethanolamide as a Hepatoprotective Agent. *Hepatology*, 50(1), pp. 143-154.

Chamulitrat, W. et al., 2012. Hepatoprotectant ursodeoxycholyl lysophosphatidylethanolamide increasing phosphatidylcholine levels as a potential therapy of acute liver injury. *Front Phys*, 3(24), pp. 1-8.

Guo, W. et al., 1993. Phospholipid impregantion of abdominal rubber drains: resistance to bacterial adherence but no effect on drain-induced bacterial translocation. *Res. Exp. Med.*, 193(5), pp. 285-296.

Hicks, A. M. et al., 2006. Unique molecular signatures of glycerophospholipid species in different rat tissues analyzed by tandem mass spectometry. *Biochim. Biophys. Acta.*, Issue 6, pp. 1022-1020.

Hills, B. A., 1993. Gastric mucosal barrier: Evidence for *heliobacter pylori* ingesting gastric surfactant and deriving protection from it. *Gut*, Issue 34, pp. 588-593.

Hills, B. A., 2002. Surface-acting phospholipid: a Pandora's box of clinical applications. Part II. Barrier and lubricating properties. *Intern. Med. J.*, Issue 32, pp. 242-251.

Istivan, T. S. & Coloe, P. S., 2006. Phospholipase A in Gram-negative bacteria and its role in pathogenesis. *Microbiology*, Volume 152, pp. 1263-1274.

Johansson, M. E., Holmén Larsson, J. M. & Hansson, G. C., 2011. The two mucus layers of colon are organized by the MUC2 mucin, whereas the outer layer is a legislator of host-microbial interactions. *Proc Natl Acad Sci USA.*, Volume 108, pp. 4659-4665.

Kramer, R. M., Roberts, E. F., Manetta, J. & Putnam, J. E., 1991. The Ca2+-sensitive cytosolic phospholipase A$_2$ is a 100-kDa protein in human monoblast U937 cells. *J Biol Chem*, Volume 266, pp. 5268-72.

Krimsky et al. (2003). Amelioration of TNBS-induced colon inflammation in rats by phospholipase A2 inhibitor. *Gastrointestinal and Liver Physiology*, 285(3), pp. G586-G592

Linkous, A. & Yazlovitskaya, E., 2010. Cytosolic phospholipase A2 as a mediator of disease pathogenesis. *Cell Microbiol*, 12(10), pp. 1369-1377.

Matoba, Y., Katsube, Y. & Sugiyama, M., 2002. The crystal structure of prokayotic phospholipase A2. *J Biol Chem*, 277(22), pp. 10059-20069.

Matoba, Y. & Sugiyama, M., 2003. Atomic resolution structure of prokaryotic phospholipase A2: analysis of internal motion and implication for a catalytic mechanism. *Proteins*, 51(3), pp. 453-69.

Murakami, M., Taketomi, Y., Sato, H. & Yamamoto, K., 2011. Secreted phospholipase A2 revisited. *J Biochem*, 150(3), pp. 233-255.

Nevalainen, T. J., Cardoso, J. C. & Riikonen, P. T., 2012. Conserved domains and evolution of secreted phospholipases A2. *The FEBS Journal*, 279(4), pp. 636-649.

Nienaber, V. L. et al., 2000. Discovering novel ligands for macromolecules using X-ray crystallographic screening. *Nat Biotechnol*, 18(10), pp. 1105-8.

Oakley, A. J. & Wilce, M. C., 2000. Macromolecular crystallography as a tool for investigating drug, enzyme and receptor interactions. *Clin Exp Pharmacol Phys*, 27(3), pp. 145-51.

O'Hara, A. M. & Shanahan, F., 2006. The gut flora as a forgotten organ. *EMBO rep*, 7(7), pp. 688-693.

Ono, T., Yamada, K., Chikazawa, Y. & Ueno, M., 2002. Characterization of a novel inhibitor of cytosolic phospholipase A2a, pyrrophenone. *Biochem J*, Volume 363, pp. 727-735.

Pathil, A. et al., 2011. The bile acid phospholipid conjugate ursodeoxycholyl lysophosphatidylethanolamide exertes anti-fibrogenic effects and inhibits epithelial-to-mesenchymal transition by blocking. *J Hepatol*, Volume 54, pp. 545-560.

Pathil, A. et al., 2012. Ursodeoxycholyl Lysophosphatidylethanolamide Improves Steatosis and Inflammation in Murine Models of Nonalcoholic Fatty Liver Disease. *Hepatology*, pp. 1369-1378.

Pathil, A., Warth, A., Chamulitrat, W. & Stremmel, W., 2012. Comparison of different bile-acid phospholipid conjugates in Acute Hepatitis. *Eur J Clin Invest*, Volume 42, pp. 130-138.

Pathil, A., Warth, A., Chamulitrat, W. & Stremmel, W., 2010. The synthetic bile acid-phospholipid conjugate ursodeoxycholyl lysophosphatidylethanolamide suppresses TNFalpha-induced liver injury. *J Hepatol*, Volume 10, pp. 674-684.

Reynolds, L. J., Hughes, L. L. & Dennis, E. A., 1992. Analysis of human synovial fluid phospholipase A$_2$ on short chain phosphatidylcholine-mixed micelles: development of a spectrophotometric assay suitable for a microtiterplate reader. *Anal Biochem*, Volume 204, pp. 190-197.

Reynolds, R. J., Hughes, L. L., Yu, L. & Dennis, E. A., 1994. 1-Hexadecyl-2-arachidonoylthio-2-deoxy-sn-glycero-3-phosphocholine as a substrate for the microtiterplate assay of human cytosolic phospholipase A2. *Anal Biochem*, Volume 217, pp. 25-32.

Sanders, W. L. et al., 2004. Discovery of potent inhibitors of dihydroneopterin aldolase using CrystaLEAD high-throughput X-ray crystallographic screening and structure-directed lead optimization. *J Med Chem*, pp. 1709-18.

Sawai, T. et al., 2000. The effect of phospholipase A$_2$ on bacterial trabslocation in a cell culture model. *Pediatr Surg Int.* pp. 262-266

Schmiel, D. & Miller, V. L., 1999. Bacterial phospholipases and pathogenesis. *Microbes and Infection*, Volume 1, pp. 1103-1112.

Schneider, H. et al., 2010. Lipid Based Therapy for Ulcerative Colitis—Modulation of Intestinal Mucus Membrane Phospholipids as a Tool to Influence Inflammation. *Int J Mol Sci*, Volume 11, pp. 4149-4164.

Sidebotham, R. L., Batten, J. J. & Karim, Q. N., 1991. Breakdown of the gastric mucus in the presence of *heliobacter pylori*. *J Clin Pathol*, Issue 44, pp. 52-57.

Street, I. P., Lin, H. K., Laliberté, F. & Ghomashchi, F., 1993. Slow- and tight-binding inhibitors of the 85-kDa human phospholipase A2. *Biochem*, Volume 32, pp. 5935-40.

Stremmel, W. & Staffer, S., 2012. *Phospholipase A2 controls the membrane fatty acid uptake complex in hepatocytes*. s.l., s.n.

Stremmel, W., Staffer, W., Pathil, A. & Chamilitrat, W., 2012. The CD36 mediated uptake of fatty acids in hepatocytes is coupled to membrane bound PLA2: the novel synthetic bile acid-phospholipid conjugate (UDCA-LPE) as pathfinder of an unexpected fatty acid uptake mechanism. *Hepatol*.

Sugiyama, M. et al., 2002. A novel prokayotic phospholipase A2. *J Biol Chem*, 277(22), pp. 20051-20058.

Torres, M. I. & Rios, A., 2008. Current view of the immunopathogenesis in inflammatory bowel disease and its implications for therapy. *W J Gastroent,* 14(13), pp. 1972-1980.

Triantafillidis, J. K., Merikas, E. & Georgopoulos, F., 2011. Current and emerging drugs for the treatment of inflammatory bowel diseases. *Drug Des Dev Ther, Volume* 5, pp. 185-210.

Triggiani, M. D., Francescopaolo, G., Giannattasio, G. & Marone, G., 2005. Secretory phospholipases $A_2$ in inflammatory and allergic diseases: Not just enzymes. *J Allergy Clin Immunol,* 118(5), pp. 1000-6.

Turner, J. R., 2009. Intestinal mucosal barrier function in health and disease. *Nat Rev Immunol,* Volume 9, pp. 799-809.

Willumeit, R. et al., 2007. Phospholipids as implant coatings. *J. Mater Med.,* Issue 2, pp. 367-380.

Zhang, Y. et al., 2011. Expression, purification, and refolding of active human and mouse secreted group IIE phospholipase $A_2$. *Protein Expr Purif,* 80(1), pp. 68-73.

US 2007/0117779

WO 2012/073245

The invention claimed is:

1. A method for inhibiting bacterial phospholipase $A_2$ and phospholipase C in a subject, the method comprising the step of:
   (a) administering to the subject an effective amount of a pharmaceutical composition comprising a lysophospholipid-conjugate; and
   (b) inhibiting bacterial phospholipase $A_2$ and phospholipase C.

2. The method according to claim 1, wherein the the subject has an inflammatory bacterial disease of the intestine.

3. The method according to claim 2, wherein the inflammatory bacterial disease of the intestine is invasive.

4. The method according to claim 2, wherein the intestine is the large intestine.

5. The method according to claim 1, wherein the subject is a mammal.

6. The method according to claim 2, wherein the inflammatory bacterial disease is selected from the group consisting of appendicitis, pseudoappendicits, ulcerative colitis, Crohn's disease, enterohemorrhagic colitis, pseudomembranous colitis, collagenous colitis, lymphocytte colitis, ischemic colitis, diversion colitis, microscopic colitis, Behçet's disease, indeterminate colitis, diverticulitis, megacolon, toxic megacolon, and enterocolitis.

7. The method according to claim 1, wherein the lysophospholipid-conjugate comprises a lysophospholipid chemically coupled to a bile acid.

8. The method according to claim 7, wherein the bile acid is ursodeoxycholate or deoxycholate.

9. The method according to claim 1, wherein the lysophospholipid-conjuaate comprises lysophosphatidylethanolamine or lysophosphatidylcholine.

10. The method according to claim 1, wherein the method further comprises the step of:
    (c) administering to the subject one or more agents selected from the group consisting of an antibiotic, an anti-inflammatory agent, an immunosuppressive agent, and an anti-diarrheal agent.

11. The method according to claim 10, wherein the one or more agents are administered prior to, simultaneously, or after step (a).

12. The method according to claim 1, wherein the pharmaceutical composition further comprises a pharmaceutically acceptable carrier, diluent or excipient.

13. The method according to claim 10, wherein the lysophospliolipid-conjugate and the one or more agents are administered as combination therapy.

* * * * *